US011311470B2

(12) United States Patent
Smith, III et al.

(10) Patent No.: US 11,311,470 B2
(45) Date of Patent: *Apr. 26, 2022

(54) CONCENTRATED PERSONAL CLEANSING COMPOSITIONS AND METHODS

(71) Applicant: The Procter & Gamble Company, Cincinnati, OH (US)

(72) Inventors: Edward Dewey Smith, III, Mason, OH (US); Shawn David McConaughy, Cincinnati, OH (US); Jianjun Justin Li, West Chester, OH (US); Marc Adam Flickinger, West Chester, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/141,581

(22) Filed: Jan. 5, 2021

(65) Prior Publication Data

US 2021/0128434 A1 May 6, 2021

Related U.S. Application Data

(63) Continuation of application No. 15/135,648, filed on Apr. 22, 2016, now abandoned.

(60) Provisional application No. 62/151,886, filed on Apr. 23, 2015.

(51) Int. Cl.
| | | |
|---|---|---|
| A61K 8/00 | (2006.01) | |
| A61K 8/46 | (2006.01) | |
| A61K 8/34 | (2006.01) | |
| A61Q 19/10 | (2006.01) | |
| A61K 8/04 | (2006.01) | |
| A61Q 13/00 | (2006.01) | |
| A61K 8/06 | (2006.01) | |
| A61K 8/44 | (2006.01) | |
| A61Q 5/02 | (2006.01) | |

(52) U.S. Cl.
CPC .............. *A61K 8/463* (2013.01); *A61K 8/042* (2013.01); *A61K 8/068* (2013.01); *A61K 8/345* (2013.01); *A61K 8/442* (2013.01); *A61Q 5/02* (2013.01); *A61Q 13/00* (2013.01); *A61Q 19/10* (2013.01)

(58) Field of Classification Search
CPC ......... A61K 8/463; A61K 8/042; A61K 8/068
See application file for complete search history.

(56) References Cited

U.S. PATENT DOCUMENTS

| | | |
|---|---|---|
| 2,438,091 A | 3/1948 | Lynch |
| 2,528,378 A | 10/1950 | McCabe, Jr. |
| 2,658,072 A | 11/1953 | Kosmin |
| 2,758,072 A | 8/1956 | Sutherland |
| 3,962,150 A | 6/1976 | Viola |
| 4,728,006 A | 3/1988 | Drobish |
| 4,747,977 A | 5/1988 | Whitehead |
| 4,997,641 A | 3/1991 | Hartnett et al. |
| 5,057,241 A | 10/1991 | Merritt et al. |
| 5,104,646 A | 4/1992 | Bolich, Jr. |
| 5,106,609 A | 4/1992 | Bolich, Jr. |
| 5,106,613 A | 4/1992 | Hartnett et al. |
| 5,252,555 A | 10/1993 | Dartnell et al. |
| 5,308,526 A | 5/1994 | Dias |
| 5,346,639 A | 9/1994 | Hatfield |
| 5,374,614 A * | 12/1994 | Behan .................... A61K 8/062 512/3 |
| 5,409,630 A | 4/1995 | Lysy et al. |
| 5,415,857 A | 5/1995 | Robbins et al. |
| 5,449,763 A | 9/1995 | Wulff et al. |
| 5,468,725 A | 11/1995 | Guenin et al. |
| 5,507,970 A | 4/1996 | Ishikawa et al. |
| 5,580,848 A | 12/1996 | Drapier |
| 5,585,343 A | 12/1996 | Mcgee et al. |
| 5,597,792 A | 1/1997 | Klier et al. |
| 5,747,436 A | 5/1998 | Patel et al. |
| 5,804,538 A | 9/1998 | Wei |
| 5,839,614 A | 11/1998 | Brown |
| 5,977,036 A | 11/1999 | Guskey |
| 6,048,834 A | 4/2000 | Drapier et al. |
| 6,074,996 A | 6/2000 | Elliott et al. |
| 6,107,261 A | 8/2000 | Taylor et al. |
| 6,136,771 A | 10/2000 | Taylor et al. |
| 6,204,230 B1 | 3/2001 | Taylor et al. |
| 6,268,330 B1 | 7/2001 | Leonard et al. |
| 6,271,187 B1 | 8/2001 | Hodge |
| 6,303,109 B1 | 10/2001 | Foerster |
| 6,329,331 B1 | 12/2001 | Aronson et al. |
| 6,358,906 B1 | 3/2002 | Ochs et al. |
| 6,362,155 B1 | 3/2002 | Kinscherf |

(Continued)

FOREIGN PATENT DOCUMENTS

| | | |
|---|---|---|
| CA | 2110951 A1 | 6/1994 |
| CA | 2196774 A1 | 2/1996 |

(Continued)

OTHER PUBLICATIONS

All final and non-final office actions for U.S. Appl. No. 15/299,722.
All final and non-final office actions for U.S. Appl. No. 15/435,533.
All final and non-final office actions for U.S. Appl. No. 15/787,832.
All final and non-final office actions for U.S. Appl. No. 16/862,666.
All Office Actions, U.S. Appl. No. 15/135,627.
All Office Actions, U.S. Appl. No. 15/135,648.
All Office Actions, U.S. Appl. No. 15/135,659.
All Office Actions, U.S. Appl. No. 15/135,675.
All Office Actions, U.S. Appl. No. 15/135,687.
All Office Actions, U.S. Appl. No. 15/135,697.

(Continued)

*Primary Examiner* — Necholus Ogden, Jr.
(74) *Attorney, Agent, or Firm* — John G. Powell

(57) ABSTRACT

Rinse-off cleansing compositions can include surfactant, perfume, solvent, and water, wherein the rinse-off cleansing composition has a G' of at least about 25 Pa and/or is not a ringing gel.

15 Claims, No Drawings

(56) References Cited

U.S. PATENT DOCUMENTS

| | | |
|---|---|---|
| 6,405,901 B1 | 6/2002 | Schantz |
| 6,429,177 B1 | 8/2002 | Williams et al. |
| 6,440,907 B1 | 8/2002 | Santora |
| 6,491,933 B2 | 12/2002 | Lorenzi et al. |
| 6,806,249 B2 | 10/2004 | Yang |
| 6,936,578 B2 | 8/2005 | Cordellina et al. |
| 6,977,082 B2 * | 12/2005 | Seitz, Jr. ............. A01N 31/08 424/401 |
| 6,998,382 B2 | 2/2006 | Yang et al. |
| 7,094,739 B2 | 8/2006 | Kessler et al. |
| 7,115,535 B1 | 10/2006 | Smith et al. |
| 7,132,468 B2 | 11/2006 | Tepe |
| 7,608,575 B2 | 10/2009 | Panandiker |
| 7,704,932 B2 | 4/2010 | Evans |
| 7,874,466 B2 | 1/2011 | Mcconville |
| 7,879,780 B2 | 2/2011 | Tsaur |
| 7,884,061 B1 | 2/2011 | Hermanson |
| 8,008,239 B2 | 8/2011 | Anantaneni et al. |
| 8,114,826 B1 | 2/2012 | Hermanson et al. |
| 8,207,100 B1 | 6/2012 | Hermanson et al. |
| 8,207,101 B1 | 6/2012 | Yang et al. |
| 8,236,747 B2 | 8/2012 | Holzhauer et al. |
| 8,263,096 B2 | 9/2012 | Myers |
| 8,408,432 B2 | 4/2013 | Delamare |
| 8,461,099 B2 | 6/2013 | Fraser et al. |
| 8,672,195 B2 | 3/2014 | Py |
| 8,697,622 B2 | 4/2014 | Man |
| 8,840,871 B2 | 9/2014 | Wei |
| 8,899,449 B2 | 12/2014 | Daansen |
| 8,937,102 B2 | 1/2015 | Hessel et al. |
| 9,254,498 B2 | 2/2016 | Daansen |
| 9,271,908 B2 | 3/2016 | Allef |
| 9,849,309 B2 | 12/2017 | Bouzeloc |
| 10,675,231 B2 | 6/2020 | Smyth |
| 10,806,686 B2 | 10/2020 | Smyth |
| 10,952,949 B2 | 3/2021 | Smith, III et al. |
| 10,952,950 B2 | 3/2021 | Smith, III et al. |
| 2001/0056049 A1 | 12/2001 | Aronson |
| 2002/0034489 A1 | 3/2002 | Wiegland et al. |
| 2003/0180246 A1 | 9/2003 | Frantz |
| 2004/0074924 A1 | 4/2004 | Kuhn |
| 2005/0019299 A1 | 1/2005 | Librizzi et al. |
| 2005/0020468 A1 | 1/2005 | Frantz |
| 2005/0042192 A1 | 2/2005 | Evans |
| 2005/0250658 A1 | 11/2005 | Putman |
| 2006/0035807 A1 | 2/2006 | Kasturi |
| 2006/0078525 A1 | 4/2006 | Tomokuni |
| 2006/0084589 A1 | 4/2006 | Vlad |
| 2006/0183662 A1 | 8/2006 | Crotty et al. |
| 2007/0027050 A1 | 2/2007 | Crotty et al. |
| 2007/0093404 A1 | 4/2007 | Gross |
| 2007/0110700 A1 | 5/2007 | Wells |
| 2007/0114246 A1 | 5/2007 | Awbrey |
| 2007/0289613 A1 | 12/2007 | Geary |
| 2008/0003247 A1 | 1/2008 | Shick |
| 2008/0032909 A1 | 2/2008 | De et al. |
| 2008/0118591 A1 | 5/2008 | Natsch |
| 2008/0139434 A1 | 6/2008 | Basappa |
| 2008/0153929 A1 | 6/2008 | Miyahara |
| 2009/0095775 A1 | 4/2009 | Domoy |
| 2009/0155383 A1 | 6/2009 | Kitko et al. |
| 2009/0221463 A1 | 9/2009 | Kitko |
| 2009/0312224 A1 | 12/2009 | Yang |
| 2010/0136175 A1 | 6/2010 | Skiff |
| 2010/0285155 A1 | 11/2010 | Gilbard |
| 2011/0152146 A1 | 6/2011 | Denutte et al. |
| 2011/0152147 A1 | 6/2011 | Smets |
| 2011/0212879 A1 | 9/2011 | Madden |
| 2011/0268778 A1 | 11/2011 | Dihora |
| 2011/0269657 A1 | 11/2011 | Dihora |
| 2011/0269658 A1 | 11/2011 | Dihora |
| 2011/0280823 A1 | 11/2011 | Madden |
| 2011/0281827 A1 | 11/2011 | Tamarkin et al. |
| 2011/0287073 A1 | 11/2011 | Strauss et al. |
| 2012/0015009 A9 | 1/2012 | Taylor |
| 2012/0091218 A1 | 4/2012 | Mikkelsen et al. |
| 2012/0114819 A1 | 5/2012 | Ragnarsson |
| 2012/0208898 A1 | 8/2012 | Dong et al. |
| 2012/0212879 A1 | 8/2012 | Li et al. |
| 2012/0316095 A1 | 12/2012 | Wei |
| 2013/0012601 A1 | 1/2013 | Hessel |
| 2013/0029932 A1 | 1/2013 | Kachi |
| 2013/0045306 A1 | 2/2013 | De |
| 2013/0053295 A1 | 2/2013 | Kinoshita et al. |
| 2013/0075430 A1 | 3/2013 | Ragnarsson |
| 2013/0230610 A1 | 9/2013 | Redmond et al. |
| 2013/0267451 A1 | 10/2013 | Hardy |
| 2014/0017386 A1 | 1/2014 | Ragnarsson |
| 2014/0162979 A1 | 6/2014 | Palla-venkata |
| 2014/0219946 A1 | 8/2014 | Hloucha |
| 2014/0263443 A1 | 9/2014 | Furusawa |
| 2014/0371128 A1 | 12/2014 | Hotz et al. |
| 2015/0057208 A1 | 2/2015 | Frantz et al. |
| 2015/0203799 A1 | 7/2015 | Bettiol et al. |
| 2015/0237905 A1 | 8/2015 | Ragnarsson |
| 2015/0272197 A1 | 10/2015 | Swain |
| 2015/0298875 A1 | 10/2015 | Dagnelie |
| 2015/0322374 A1 | 11/2015 | Tchakalova |
| 2015/0359725 A1 | 12/2015 | Glenn, Jr. |
| 2015/0359726 A1 | 12/2015 | Glenn, Jr. |
| 2015/0359727 A1 | 12/2015 | Glenn, Jr. |
| 2015/0359728 A1 | 12/2015 | Glenn, Jr. |
| 2016/0128917 A1 | 5/2016 | Wei |
| 2016/0128927 A1 | 5/2016 | Wei et al. |
| 2016/0143821 A1 | 5/2016 | Chang |
| 2016/0167864 A1 | 6/2016 | De Cleir |
| 2016/0309871 A1 | 10/2016 | Torres Rivera et al. |
| 2016/0310369 A1 | 10/2016 | Thompson |
| 2016/0310370 A1 | 10/2016 | Zhao |
| 2016/0310371 A1 | 10/2016 | Zhao |
| 2016/0310372 A1 | 10/2016 | Glenn, Jr. |
| 2016/0310375 A1 | 10/2016 | Torres Rivera |
| 2016/0310376 A1 | 10/2016 | Torres Rivera |
| 2016/0310377 A1 | 10/2016 | Torres Rivera |
| 2016/0310386 A1 | 10/2016 | Smith, III et al. |
| 2016/0310387 A1 | 10/2016 | Smith, III |
| 2016/0310388 A1 | 10/2016 | Smith, III |
| 2016/0310389 A1 | 10/2016 | Thompson |
| 2016/0310390 A1 | 10/2016 | Smith, III |
| 2016/0310391 A1 | 10/2016 | Smith, III |
| 2016/0310392 A1 | 10/2016 | Smith, III |
| 2016/0310393 A1 | 10/2016 | Chang |
| 2016/0310397 A1 | 10/2016 | Johnson |
| 2016/0310402 A1 | 10/2016 | Zhao |
| 2016/0354300 A1 | 12/2016 | Thompson |
| 2016/0374932 A1 | 12/2016 | Song |
| 2017/0087068 A1 | 3/2017 | Callens |
| 2017/0165155 A1 | 6/2017 | Glenn, Jr. |
| 2017/0165156 A1 | 6/2017 | Glenn, Jr. |
| 2017/0165157 A1 | 6/2017 | Glenn, Jr. |
| 2017/0165162 A1 | 6/2017 | Glenn, Jr. |
| 2017/0165163 A1 | 6/2017 | Glenn, Jr. |
| 2017/0165164 A1 | 6/2017 | Zhao et al. |
| 2017/0165165 A1 | 6/2017 | Zhao et al. |
| 2017/0165191 A1 | 6/2017 | Glenn, Jr. |
| 2017/0174413 A1 | 6/2017 | Callens |
| 2017/0246101 A1 | 8/2017 | Iwata |
| 2017/0278249 A1 | 9/2017 | Stofel et al. |
| 2017/0304172 A1 | 10/2017 | Chang |
| 2017/0304184 A1 | 10/2017 | Glenn, Jr. |
| 2017/0304185 A1 | 10/2017 | Glenn, Jr. |
| 2017/0304186 A1 | 10/2017 | Glenn, Jr. |
| 2018/0110688 A1 | 4/2018 | Torres Rivera |
| 2018/0110689 A1 | 4/2018 | Torres Rivera |
| 2018/0110690 A1 | 4/2018 | Torres Rivera et al. |
| 2018/0110691 A1 | 4/2018 | Torres Rivera |
| 2018/0110692 A1 | 4/2018 | Torres Rivera |
| 2018/0110693 A1 | 4/2018 | Renock |
| 2018/0110694 A1 | 4/2018 | Renock |
| 2018/0110695 A1 | 4/2018 | Thompson et al. |
| 2018/0110696 A1 | 4/2018 | Johnson |
| 2018/0110697 A1 | 4/2018 | Smith, III |
| 2018/0110704 A1 | 4/2018 | Zhao |
| 2018/0110707 A1 | 4/2018 | Zhao |

(56) References Cited

U.S. PATENT DOCUMENTS

| | | | |
|---|---|---|---|
| 2018/0110709 | A1 | 4/2018 | Smyth |
| 2018/0110710 | A1 | 4/2018 | Zhao |
| 2018/0110714 | A1 | 4/2018 | Glenn, Jr. |
| 2018/0235861 | A1 | 8/2018 | Smyth |
| 2018/0235862 | A1 | 8/2018 | Smyth |
| 2020/0253850 | A1 | 8/2020 | Smyth |
| 2021/0128434 | A1 | 5/2021 | Smith, III et al. |
| 2021/0169763 | A1 | 6/2021 | Smith, III et al. |

FOREIGN PATENT DOCUMENTS

| | | |
|---|---|---|
| CA | 2631077 C | 3/2015 |
| CN | 1252263 A | 5/2000 |
| CN | 101039651 A | 9/2007 |
| CN | 101193619 A | 6/2008 |
| CN | 102258440 A | 11/2011 |
| CN | 103893060 A | 7/2014 |
| DE | 4315396 A1 | 11/1994 |
| DE | 19624051 A1 | 12/1997 |
| EP | 0316726 A2 | 5/1989 |
| EP | 0368146 A2 | 5/1990 |
| EP | 0232153 B1 | 8/1994 |
| EP | 0743310 A1 | 11/1996 |
| EP | 0780464 B1 | 4/2003 |
| EP | 1714678 A1 | 10/2006 |
| EP | 1859777 A2 | 11/2007 |
| EP | 2042216 B1 | 9/2015 |
| FR | 2998476 A1 | 5/2014 |
| GB | 2223236 B | 9/1992 |
| GB | 2280682 A | 2/1995 |
| GB | 2284215 A | 5/1995 |
| GB | 2351979 A | 1/2001 |
| GB | 2371307 A | 7/2002 |
| JP | 9194877 A | 7/1997 |
| JP | H1018177 A | 1/1998 |
| JP | H1053795 A | 2/1998 |
| JP | 10182366 A | 7/1998 |
| JP | 2000212031 A | 8/2000 |
| JP | 2001213762 A | 8/2001 |
| JP | 200445869 | 12/2004 |
| JP | 3644658 B2 | 2/2005 |
| JP | 2007320884 A | 12/2007 |
| JP | 2010138348 A | 6/2010 |
| JP | 2010150315 A | 7/2010 |
| JP | 2012001597 A | 1/2012 |
| JP | 4915720 B2 | 2/2012 |
| JP | 4965869 B2 | 4/2012 |
| JP | 5465872 B2 | 1/2014 |
| WO | 9418946 A1 | 9/1994 |
| WO | 9612787 A1 | 5/1996 |
| WO | 9616160 A1 | 5/1996 |
| WO | 9730688 A1 | 8/1997 |
| WO | 9748378 A1 | 12/1997 |
| WO | 9806817 A1 | 2/1998 |
| WO | 200062755 A1 | 10/2000 |
| WO | 0076460 A2 | 12/2000 |
| WO | 0137658 A2 | 5/2001 |
| WO | 0142409 A1 | 6/2001 |
| WO | 02066589 A2 | 8/2002 |
| WO | 02092050 A2 | 11/2002 |
| WO | 02097020 A2 | 12/2002 |
| WO | 2004045576 A1 | 6/2004 |
| WO | 2008110995 A2 | 9/2008 |
| WO | 2010052070 A2 | 5/2010 |
| WO | 2010052071 A2 | 5/2010 |
| WO | 2010052147 A2 | 5/2010 |
| WO | 2011049932 A1 | 4/2011 |
| WO | 2011094714 A1 | 8/2011 |
| WO | 2012055855 A1 | 5/2012 |
| WO | 2013007473 A2 | 1/2013 |
| WO | 2013163074 A1 | 10/2013 |
| WO | 2014090959 A1 | 6/2014 |
| WO | 2016026777 A1 | 2/2016 |
| WO | 2016077114 A1 | 5/2016 |
| WO | 2016149166 A1 | 9/2016 |
| WO | 2016172405 A1 | 10/2016 |
| WO | 2016172468 A1 | 10/2016 |
| WO | 2016172472 A1 | 10/2016 |
| WO | 2016172475 A1 | 10/2016 |
| WO | 2016172478 A1 | 10/2016 |
| WO | 2016172482 A1 | 10/2016 |
| WO | 2018075749 A1 | 4/2018 |

OTHER PUBLICATIONS

Dow—Methocel Cellulose Ethers Technical Handbook, p. 1-32, Jun. 1997.
Dow—Personal Care Solutions, Cellulosic Thickeners Product Selection Guide, p. 1-2, Feb. 2015.
International Search Report and Written Opinion of the International Searching Authority, PCT/US2016/028827, dated Jul. 28, 2016, 10 pages.
International Search Report and Written Opinion of the International Searching Authority, PCT/US2016/028832, dated Jun. 15, 2016, 10 pages.
International Search Report and Written Opinion of the International Searching Authority, PCT/US2016/028835, dated Jul. 27, 2016, 10 pages.
International Search Report and Written Opinion of the International Searching Authority, PCT/US2016/028840, dated Jul. 27, 2016, 10 pages.
International Search Report and Written Opinion of the International Searching Authority, PCT/US2016/028843, dated Jul. 27, 2016, 10 pages.
International Search Report and Written Opinion of the International Searching Authority, PCT/US2016/028846, dated Jul. 27, 2016, 10 pages.
International Search Report and Written Opinion of the International Searching Authority, PCT/US2017/057354, dated Jan. 5, 2018, 11 pages.
International Search Report and Written Opinion of the International Searching Authority, PCT/US2017/057555, dated Nov. 20, 2017, 13 pages.
International Search Report and Written Opinion of the International Searching Authority, PCT/US2018/017738, dated May 9, 2018, 13 pages.
International Search Report and Written Opinion of the International Searching Authority, PCT/US2018/017741, dated May 9, 2018, 12 pages.
PCT International Search Report and Written Opinion for PCT/US2016/066752 dated Feb. 22, 2017.
All final and non-final office actions for U.S. Appl. No. 17/176,404.
All Office Actions, U.S. Appl. No. 15/435,546.
All Office Actions, U.S. Appl. No. 17/176,417.
Oetter et al., Ringing Gels and their Fascinating Properties, Colloids and Surfaces, vol. 38, 1989, pp. 225-250.
PLUS Search generated internally by the US PTO support staff for this application attached and requested using STIC internal services, Feb. 24, 2021 (Year: 2021).
STIC Search Report generated by the US PTO support staff for this application (Chen Haoyi) attached and requested, Feb. 25, 2021, 16 pages.

* cited by examiner

CONCENTRATED PERSONAL CLEANSING COMPOSITIONS AND METHODS

FIELD OF THE INVENTION

This application relates to rinse-off cleansing compositions with surfactant, perfume, solvent, and water; and methods relating thereto.

BACKGROUND OF THE INVENTION

Cleansing is an activity that has been done for thousands of years. Early cleansers were based on either soap chemistry or simple mechanical action in order to remove dirt from the skin, as well as endogenous soils such as sweat, sebum and body odors. Smelling clean is an important benefit but early cleansers did not provide perfume to the skin during cleansing as it would have been wasteful for a very expensive ingredient, the perfume. Instead, perfume was applied after cleansing. As skin cleansing compositions have become more complex, providing scent during cleansing and residual scent on the skin after cleansing are expected by users of modern skin cleansers. As such, improved cleansing compositions which can provide scent during cleansing and/or residual scent on the skin are desired.

SUMMARY OF THE INVENTION

A rinse-off cleansing composition, comprising: a) from about 20% to about 34%, by weight of the composition, of surfactant; b) from about 4% to about 30%, by weight of the composition, of a perfume, wherein the weight percent of perfume is from about 10% to about 90%, by weight of the surfactant; c) from about 3% to about 20%, by weight of the composition, of a solvent, wherein at least 3% of the solvent, by weight of the composition, comprises a hydric solvent and wherein the weight percent of the hydric solvent is from about 8% to about 60%, by weight of the surfactant; and d) from about 10% to about 73%, by weight of the composition, of water; wherein the rinse-off cleansing composition has a G' at 1 Hz of about 25 Pa to about 3000 Pa.

A rinse-off cleansing composition, comprising: a) from about 15% to about 20%, by weight of the composition, of a first surfactant comprising a branched anionic surfactant; b) from about 4% to about 10%, by weight of the composition, of a perfume; c) from about 4% to about 10%, by weight of the composition, of dipropylene glycol; and d) from about 50% to about 70%, by weight of the composition, of water; wherein the composition is not a ringing gel.

A cleansing composition, consisting essentially of: a) from about 15% to about 25%, by weight of the composition, of a first surfactant comprising a branched anionic surfactant; b) from about 4% to about 10%, by weight of the composition, of a zwitterionic cosurfactant; c) from about 4% to about 10%, by weight of the composition, of a perfume; d) from about 4% to about 10%, by weight of the composition, of dipropylene glycol; e) optionally from about 0.1% to about 5% of a preservative, thickener, hydrophobic oil, additive, soap, or a combination thereof; and from about 30% to about 70%, by weight of the composition, of water; wherein the rinse-off cleansing composition is not a ringing gel.

These and other compositions will be more fully understood in light of the detailed description below.

DETAILED DESCRIPTION OF THE INVENTION

I. Definitions

As used herein, the following terms shall have the meaning specified thereafter:

"Cleansing composition" refers to compositions intended for topical application to the skin or hair for cleansing.

"Concentrate/concentrated" as used herein with respect to a cleansing composition refers to a composition where the weight percentage of surfactant relative to the total composition is greater than about 15%.

"Free of" refers to no detectable amount of the stated ingredient or thing.

"Gel" refers to a material or composition that does not flow under its own weight and has a G' greater than about 25 Pa at 10 Hz in an oscillatory rheology test.

"Hydric solvent" refers to a solvent that is neutral organic species that contains at least 2 hydroxyl groups and is not a hydrotrope.

"Hydrotrope" refers to a charged, amphiphilic solubility modifier. Hydrotropes are generally charged olefins especially an olefin sulfonate such as an aromatic sulfonate.

"In-vitro Bloom" refers to the amount of perfume experienced at a 3:1 by weight water to composition dilution versus the amount of perfume in the headspace prior to dilution and can be measured in accordance with Perfumed Headspace Abundance During Dilution Method set out below.

"Micelle" as used herein refers to a structure comprising individual surfactant molecules aggregated to form a hydrophobic core region with externally facing polar head groups in equilibrium with surfactant monomers in a polar phase, having a characteristic dimension that is a single digit multiple of the surfactant length, i.e., generally less than about 10 nm in diameter.

"Microemulsion" as used herein refers to a thermodynamically stable isotropic mixture of oil, surfactant, and water comprising an interior hydrophobic core, having a size greater than about 10 nm diameter.

"Perfume" refers to a mixture of volatile organic oils having a pleasant aroma wherein the perfume components have individual molecular weights between about 75 and 400 Daltons.

"Relative Bloom" refers to perfume in the headspace over a composition during use for a perfumed cleansing composition relative to concentration for a conventional, hydric solvent free, control micelle composition having 10 wt % starting surfactant and 1 wt % starting perfume when the same perfume is used in the composition and the micelle composition.

"Rinse-off" means the intended product usage includes application to skin and/or hair followed by rinsing and/or wiping the product from the skin and/or hair within a few seconds to minutes of the application step. The product is generally applied and rinsed in the same usage event, for example, a shower.

"Room temperature" refers to a temperature of 25° C.

"Solvent" refers to species or mixture of species present in a molecular solution in the greatest molar concentration acting in a way to dissolve other species, the latter species generally being larger molecules. A "hydric solvent" is a water miscible solvent.

"Single Phase" when used herein with respect to inventive cleansing compositions refers to homogeneity when measured at the designated temperature in accordance with the Ultracentrifuge Test.

"Stable" when used herein with respect to the inventive cleansing compositions refers to visual stability when measured in accordance with the Stability Test herein.

"Substantially free of" refers to about 2% or less, about 1% or less, or about 0.1% or less of a stated ingredient.

"Surfactant" as used herein refers to amphiphilic molecules which can aggregate to form micelles and other surfactant structures, which are soluble in an aqueous phase and contribute to foaming during a cleansing event, i.e., stabilizing an air interface.

II. Cleansing Compositions

Modern consumers of cleansing compositions expect the composition to provide scent both during use and to have residual scent on the skin after use, making perfume an important component of cleansing compositions. Perfume is also an important component of many skin cleansers to mask the base odor of cleansing ingredients, which can be unpleasant.

Perfume is hydrophobic, whereas skin cleansers generally have an aqueous, continuous phase which provides essentially no ability to carry perfume. It is desirable to provide perfume in a soluble form in a liquid skin cleanser, since insoluble phases of any kind can lead to instability problems in the composition. Perfume is therefore generally solubilized within the surfactant component of cleansers, such as micelles, lamellar structures, vesicles and the like. Surfactant structures of all kinds contain hydrophobic regions due to the aggregation of surfactant tails, which are able to solubilize significant quantities of perfume oil. Perfume generally exists within the surfactant tails as a molecular solution due to the interaction of the perfume with the surfactant tails, not as a colloidal structure such as an emulsion droplet, which is not thermodynamically stable.

A problem exists in providing perfume scent during use and residual scent to the skin from skin cleansers. Well known physical laws govern the relationship between perfume in the air in equilibrium with perfume solubilized in a micelle or other environment. This relationship is defined by the mole fraction of perfume in the soluble environment, generally the micelle. Micelles are common features of skin cleansers since even non-micellar surfactant generally become micelles during the dilution experienced while cleansing.

Since the perfume concentration in a skin cleanser is generally only 25% or less on a molar basis in the surfactant micelle, the vapor pressure of each perfume molecule can be reduced by 75% or even more, due to its solubilization in the micelle. The desire to deliver perfume to the skin suffers from a similar fate during cleansing. Perfume molecules can diffuse, or partition into the skin during cleansing. The driving force to do so is the thermodynamic activity coefficient gradient for the perfume molecules. While a pure perfume applied to the skin, having an activity coefficient of 1, can partition quickly into skin, perfume located in a surfactant micelle proximal to the skin suffers from the activity coefficient reduction (75% or more) due to micellar solubilization. Therefore most perfume in cleansing compositions (between 50-90%) generally is washed away during rinsing before a significant amount can partition into the skin or bloom into the headspace. The result is the skin retains no or very little scent and only for a short duration after a typical cleansing event. Thus, delivery of perfume to the air and to the skin during cleansing is inefficient and therefore expensive.

Overcoming these technical constraints in order to increase initial perfume perception in a neat composition, perfume delivery to the air during cleansing, and to the skin is not simply a matter of adjusting formula components at increased cost. Natural limits exist related to factors such as solubility. For example, increasing perfume in a composition is not only impractical from a cost standpoint, perfume being quite expensive, but is also infeasible considering the abundance of perfume can quickly become insoluble in the surfactant composition, leading to instability. Formulating a perfume to contain more high vapor pressure components to enhance bloom may be useful, but does not overcome the innate vapor pressure reduction of perfume due to solubilization in the micelle, in addition to other restrictions to the scent character that would result. Benefits of these approaches are limited.

Various means to overcome this problem have been suggested. Perfume microcapsules have been developed to encapsulate perfume and protect it from contact with surfactant. However, only a limited number of perfume molecules are stable in perfume microcapsules; and the perfume microcapsule itself must then be delivered to the skin and, later, mechanically crushed by the consumer in order to release the perfume. Most perfume microcapsules are themselves washed down the drain during cleansing, affording little benefit.

Additionally, cleansing compositions have been formulated as micelles. Surfactants have a critical micelle concentration, or CMC, at which they aggregate. Below the CMC surfactant exists as monomers in solution. It has been suggested that dilution to below the CMC can release perfume to increase bloom. The problem with this approach is the CMC is very low, often about 100 ppm for cleansing surfactant mixtures (i.e., 0.01 wt. %, a dilution of more than 500-fold from an original composition). Thus, the CMC occurs at concentrations not relevant to cleansing nor rinsing the body. During rinsing, the CMC is reached only at the very end of cleansing, by which time nearly all the cleansing components have already been washed down the drain in the form of micelles, carrying the perfume with them. Relevant dilutions during cleansing are less than 10-fold, especially less than 5-fold, during which time there is extensive exposure of the wash composition to the body and to the air in the shower, affording both time and opportunity for perfume to bloom and partition to the skin, if it can be removed from the environment of the micelle.

A constraint in overcoming these problems relates to the rheology profile of the composition. Liquid skin cleansing compositions generally require dosing from a package onto a hand, a cleansing implement, or the skin itself without running off. Further, compositions should spread easily across the body to effect thorough cleansing. Preferred means to provide an acceptable rheology involve the use of surfactants to form elongated micelles or lamellar structures without the use of other rheology control agents, which can be wasteful and costly. Control of rheology using surfactants can provide important restrictions which limit the ability to modify surfactant mixtures to provide other benefits, such as perfume benefits. Often, polymeric or associative thickening agents can be used to control rheology, but these can create new restrictions or constraints by interacting with micelles. Overcoming the problems related to perfume benefits in cleansing compositions while maintaining an acceptable rheology profile for dispensing is therefore a highly constrained problem and difficult to overcome. Control of rheology in concentrated compositions having only about 2× concentration to 3× concentration (i.e., about 15 wt % to about 35 wt % surfactant by weight of the composition) can be particularly challenging in compositions which utilize solvents to enhance perfume delivery, because the relatively low levels of surfactant minimize rheology contribution while at the same time the solvents also reduce rheology attributes such as viscosity and G' (elasticity).

Surprisingly, inventors have discovered skin cleansing compositions can deliver enhanced initial perfume perception, perfume bloom during cleansing, and perfume retention on the skin for many hours after cleansing. Without wishing to be limited by theory, the enhanced perfume benefits are believed to result at least in part when at least a portion of the perfume in a composition exists in the physical form of a perfume microemulsion. In some cases, the microemulsion may be in equilibrium with other phases such as micelles or a lamellar phase. In some cases, the microemulsion can spontaneously form upon addition of water, i.e., during cleansing or rinsing. In the microemulsion form, it is believed most perfume is in the central core region and is not proximal to surfactant hydrocarbon, therefore it is not in a solvent-solute relationship which can reduce perfume activity coefficient. The result is bloom and/or relative bloom is significantly enhanced, sometimes doubled or even tripled or more; and scent of perfume over the skin after wash, can be enhanced by a similar magnitude.

To make a perfume microemulsion, sufficiency of perfume, which is the oil component for making a perfume core; the right level and mixture of surfactant; and a hydric solvent able to interact in a manner to make the microemulsion are believed to be contributing factors. The hydric solvent has multiple effects like, reducing the dielectric of the water phase, acting as a solvent for the surfactant head groups, reducing interfacial tension between the aqueous phase and hydrocarbon, and interacting with the perfume in the core. Hydric solvents can be chameleonic in nature, able to provide miscibility with hydrophobic perfume oil and water external to the microemulsion phase. During use of the body cleansing composition, as the composition is diluted, hydric solvent can be reduced in concentration in a perfume microemulsion core because of the abundance of water added during washing and rinsing, providing a further benefit to increase perfume activity coefficient by increasing perfume molar concentration in the core. Thus, a sufficient amount of particular kinds of hydric solvents can be used to form a microemulsion phase which can increase perfume activity during use.

Some compositions may be in a lamellar phase prior to dilution during use, but can be transformed to a perfume microemulsion during use. In some cases, the transformation during dilution to a perfume microemulsion may be brief, within a restricted dilution range, but such range is sufficient to deliver perfume bloom and partitioning into the skin which, once partitioning is effected, it cannot be reversed. Certain microemulsions may be in equilibrium with other phases, such as micelles or a lamellar phase, either in the composition or during dilution of the composition during use. There may be advantages for both the microemulsion and micelle phases to coexist, since micelles may provide superior lather and cleaning properties at the same time the microemulsion may deliver enhanced perfume benefits. Certain analytical measures, such as dynamic light scattering and optical light transmission, can be used as guides, when evaluating microemulsion phases. Additionally, perfume analysis in the headspace is directly relatable to the perfume solvent environment in a composition or a diluted composition, so that gas chromatography-mass spectrometry (GCMS) headspace measures are an indicator of the perfume environment, i.e., the microemulsion phase and the perfume relationship to solvent molecules therein. Well established physical laws govern the relationship between concentration of molecules in the headspace, and the solvent environment of the molecules in solution, e.g., Raoult's Law. Likewise, headspace measurements over the skin after washing are similarly useful, since perfume partitioning into the skin is enhanced by perfume activity coefficient, as previously discussed.

When the microemulsion phase is present, increased bloom and/or relative bloom can be demonstrated by measuring the relative abundance of perfume in the headspace over the composition or comparative composition using the Perfume Headspace Abundance During Dilution Method (PHADD), which utilizes solid phase microextraction GCMS (SPME-GCMS) to collect and evaluate perfume molecules (PRM) in the headspace over a neat composition and through stepwise aqueous dilutions. Results can be compared to a control micelle composition using the same perfume. When inventive compositions form a microemulsion phase, headspace perfume concentration can more than double compared to control, sometimes providing a 3-fold or greater headspace perfume concentration compared to control. In addition, evaluation among untrained and undirected consumers confirms extraordinary noticeability of the bloom benefit.

Increased perfume retention on the skin after cleansing can be demonstrated by measuring the relative abundance of perfume in the headspace over the skin using the Perfumed Skin Headspace Abundance Method (PSHAM), which utilizes a collector in a glass dome-shaped chamber over the skin to collect perfume, followed by heat desorption and evaluation of PRM by GCMS. Relative to control micelle compositions at the same perfume dose, inventive compositions can provide more than double the scent over the skin compared to control, sometimes providing a 3-fold or greater perfume retention on skin compared to control. Evaluation among untrained and undirected consumers confirmed extraordinary noticeability of the skin retention benefit.

Dynamic Light Scattering is a useful means to detect structures in the size range of microemulsion droplets, and micelles, but the results can be difficult to interpret when more than one structure may be present, such as micelles and a microemulsion both. A bimodal scattering intensity distribution may be present in inventive compositions, suggesting micelles having a diameter generally below 10 nm in equilibrium with larger structures, which are generally greater than about 20 nm which are the perfume microemulsion droplets.

A microemulsion phase generally has a low viscosity and is a Newtonian fluid. Cleansing fluids with these viscosity characteristics are generally useful when dispensed from a package which controls the dose or spreads it onto the target surface, such as a pump foamer or a spray. To fit with current consumer habits during body cleansing, a cleansing composition can be in the form of a gel having a structure defined by an elastic modulus, G', a viscous modulus, G", a viscosity, and a shear thinning viscosity ratio as measured by the test methods below. A microemulsion composition can be concentrated to create a gel, wherein the gel provides a suitable rheology to easily dispense the composition from a package. The gel may comprise a lamellar phase, and may or may not have a high concentration of perfume in its headspace prior to being diluted, relative to a micelle composition. In some cases, when the gel has a high perfume concentration in its headspace, it is believed to be in equilibrium with a microemulsion phase, since the gel can evince a characteristic lamellar x-ray diffraction pattern. In other cases, the gel can have a high perfume concentration in the headspace only after dilution water is introduced.

The composition may be concentrated in order to create desirable rheology characteristics, i.e., a gel. Some compositions may be concentrated at least 3-fold relative to conventional body wash, which generally has about 10 wt % surfactant. When the amount of surfactant is greater than about 15 wt % of the composition, the surfactant can be considered to be concentrated and the composition can be considered to be a concentrate. Generally, a composition having about 20 wt % surfactant can be considered about a 2-fold concentrate, a composition having about 30 wt % surfactant a 3-fold concentrate, and so on.

In certain cases, increasing concentration may be preferable because a gel can be created which has both desirable rheology characteristics useful for dispensing, in addition to a sufficiency of hydric solvent to form the microemulsion phase either as a component of the gel or during dilution of the composition. Some hydric solvents can significantly reduce the viscosity and/or G' of the gel, therefore concentration can be a useful means to increase the amount of hydric solvent that can be tolerated within a composition.

Additionally, organic solvents are useful to help form a microemulsion phase. Some organic solvents are miscible in water, at least partially miscible in perfume oil, and can interact with surfactant polar head groups to reduce structure and generally reduce viscosity as a result. The microemulsion phase requires very low interfacial tension. Perfume can be essentially relegated to the core of a water continuous microemulsion phase and therefore has a high activity coefficient, which can be effected by using a hydric solvent having water, perfume oil, and surfactant miscibility to reduce interfacial tension.

Water miscibility of hydric solvent can be determined by mixing the solvent with water and measuring turbidity as an indicator of solubility. When mixtures are less than fully transparent, the mixture is no longer a molecular solution. Hydric solvents that are fully miscible with water at ambient temperature and shower temperature tend to work well in helping with microemulsion formation. A spectrophotometer can be used to measure miscibility by optical clarity, by measuring % light transmission at a visible wavelength of light such as 640 nm. Hydric solvent is added in increasing amounts to water, measuring optical clarity. When all mixtures are optically transparent, the solvent is fully water miscible. If some mixtures are less than transparent, the concentration of hydric solvent at the onset of turbidity is its aqueous solubility.

Perfume miscibility of a hydric solvent can be determined by mixing the solvent with a representative perfume or perfume molecule and measuring optical clarity. When the perfume-solvent mixture is less than fully transparent the mixture is no longer a molecular solution. Hydric solvent is added until past the point of optical clarity, using a spectrophotometer to measure % Transmission for the mixture at an optical wavelength. Perfume miscibility is defined as the highest percentage of hydric solvent that can be added to a perfume, based on the weight of the two, which remains optically clear, i.e., generally about 100% T at 640 nm (minus a small amount of absorbance, but not scattering). Exemplary hydric solvents are at least about 10%, 15%, 20%, or 40 wt % miscible in the target perfume based on total weight of the perfume-solvent mixture. When solvent is miscible with both perfume and water, surface tension between the water and perfume phases in a composition can be lower, which creates optimal conditions for the formation of a microemulsion. When miscibility with both water and perfume is even higher, i.e., as high as 100%, solvent located in a microemulsion core with perfume can rapidly migrate to the aqueous phase during product use. The abundance of additional water during cleansing thus can reduce solvent in the microemulsion perfume core, reducing its action as a perfume solvent. This increases the thermodynamic activity coefficient of the perfume allowing it to both bloom in the shower and partition into the skin to provide superior scent longevity.

Perfume miscibility of a hydric solvent can vary by perfume since each perfume has unique chemical components. Perfume miscibility can be measured for a particular solvent in a specific perfume, such as the table below demonstrates for the perfume having the components listed below and used in the first series of composition examples further below.

A perfume, perfume X, was used having these below in addition to other components, the components below were identified from the spectra, area counted and summed per the PHADD method disclosed herein. PRM (KI): Alpha pinene (940), camphene (955), myrcene (990), para-cymene (1028), d-limonene (1034), eucalyptol (1037), dihydromyrcenol (1071), alpha terpinene (1022), linalool (1107), camphor (1154), methyphenylcarbinyl acetate (1193), florol major 2 (1197), allyl amyl glycolate major (1234), linalyl acetate (1254), coranol (1275), 1H-Indene,2,3-dihydro-1,1, 2,3,3-pentamethyl (1325), neryl acetate (1364), cyclemax (1427), coumarin (1449), gamma methyl ionone (1491), butylated hydroxyl toluene (1519), cashmeran (1517), methyldihydrojasmonate (1663), cis-hexenyl salicylate (1680), Iso-E Super Major (1686), Helvetolide major (1727), ambroxan major 2 (1791), galaxolide (1874).

|  | Perfume X miscibility (% of solvent added) |
| --- | --- |
| dipropylene glycol | 100% |
| hexylene glycol | 100% |
| *PEG 300 | 57% |
| propylene glycol | 38.5% |
| 1,3-butanediol | 33.0% |
| 1,6-hexanediol | 25.1% |
| glycerine | 3.2% |

*Sentry PEG hydric ability of the hydric transparent

Dow Chemicals Carbowax 300 average molecular weight

Surfactant miscibility of a solvent can also be important to microemulsion to form. Preferred solvents can form an optically mixture when 45 parts surfactant are mixed with 30 parts hydric solvent and 25 parts water, which mixture can absorb an additional 30 parts of perfume oil while remaining optically clear.

When a hydric solvent meets these aforementioned criteria, generally a transparent microemulsion can be formed in the presence of perfume and surfactant with the solvent such that the composition can absorb at least 0.5 parts of perfume oil:surfactant while retaining optical clarity. Generally, a micelle is only capable of absorbing about 25% perfume oil by weight of the surfactant. Whereas microemulsion compositions can absorb about 50% or 75% or 100% or more, of the weight of the surfactant, in perfume oil while retaining optical clarity. In some cases, it may take a day or more for the microemulsion to spontaneously form at ambient temperature, to establish the equilibrium phase behavior.

One class of a hydric solvent that is miscible with water and many perfumes is glycol. Glycols may have a mixture of isomers. One exemplary glycol class is diols where the alcohol groups are separated by no more than 2 carbons on average. Suitable glycols can include, for example, dipropylene glycol, propylene glycol, butylene glycol, pentylene glycol, hexylene glycol, or combinations thereof. Glycols can include pure materials and mixtures of isomers. For example, hexylene glycol includes 1,6-hexane diol; 1,4-hexane diol; or methyl pentanediol structures having 2 alcohol groups, etc.

Hydric solvents can modify the rheological properties of the composition, particularly reducing the viscosity. It was previously discussed that concentrating a composition into a gel is one way to combat low viscosity to improve dispensing and spreading characteristics. These types of compositions often exhibit a classic x-ray diffraction pattern of a lamellar phase. However, when the level of hydric solvent is greater than about 40%, by weight of the surfactant, it can be difficult to form a structured gel and thus the composition can have a much lower viscosity and is difficult to dispense from conventional body wash packages. When composition with an exemplary rheology profile are desired, an intermediate level of hydric solvent can be used to deliver both exemplary rheology and perfume delivery properties. Thus, the hydric solvent can be from about 10% to about 40%, from about 12% to about 40%, from about 15% to about 35%, from about 17% to about 35%, from about 20% to about 30%, expressed as a weight percent of the surfactant.

Perfume is a benefit agent. Perfume benefits can be realized at different time points for cleansing compositions. Perfume in the package headspace can be important to select a product at the time of purchase. Perfume scent during cleansing, upon introduction of modest amounts of water, such as for example about 3 parts of water per part composition (i.e., a 3:1 dilution ratio), provides a benefit during skin cleansing. During skin cleansing, some perfume can partition into the outer layers of the skin or hair, which can provide a scented skin or hair benefit for a period of time after cleansing, called scent longevity. A governing property for both scent bloom and longevity is the activity coefficient of the perfume molecules, which is a thermodynamic term. Perfume molecules exhibit their maximum vapor pressure only when they are pure. Diluted perfume molecules, whether diluted by surfactant in a micelle, organic solvent, water, etc., exhibit less than their pure vapor pressure. The amount of perfume in a headspace over a composition, diluted composition, or over the skin or hair can be measured analytically, as described in the methods section below. Benefits in initial fragrance intensity, bloom, or longevity can be demonstrated by comparing performance of the compositions before, during, and, or after a skin or hair cleansing event, compared to conventional body wash or shampoo compositions.

In addition to being a benefit agent, perfume is an oil and therefore can be a direct contributor to formation of phases responsible for its activity coefficient (as noted above), and therefore to scent bloom and longevity benefits. As discussed above, perfume oil can generally be added into micelle surfactant mixtures only to about 0.25 weight fraction of the surfactant before it phase separates, whereas diluted cleansing compositions described herein can hold at least 0.5 parts perfume:surfactant, or even 0.75 parts perfume:surfactant, or even more, while remaining transparent, including water diluted compositions. The ability to hold large amounts of perfume in this manner while remaining transparent, isotropic and low viscosity is an indication the diluted composition is a microemulsion phase and is suitable for enhanced perfume benefits.

Perfume can be a carrier for non-scented, hydrophobic additives. Additives which are at least 5 wt %, or at least 10 wt %, or at least 20 wt % miscible with perfume may be employed to increase delivery of the additives to the skin or hair. Any additive which provides a benefit to the skin or hair or the skin environment (e.g., the skin microbiome) may be employed. The additive may provide a direct or indirect benefit, such as antibacterial, antihyperproliferative, anti-inflammatory, chelation , pH regulation, antifungal, antiviral, control of disorders such as acne, atopic dermatitis, eczema, dermatitis, dandruff, antiaging, antiwrinkle, age spot reduction, sunscreen, hydration, moisturization, or any other skin benefit. An advantage of the present compositions is enhanced additive delivery to the skin or hair during cleansing. A further benefit is reduction in activity coefficient of the additive by dilution with perfume is transient due to subsequent evaporation of the perfume on the skin, which increases the thermodynamic activity of the additive after its delivery to the skin.

In addition, some compositions may form microemulsions but perform poorly for lathering and hence cleaning, which are important features for consumers. Compositions which effectively deliver perfume as described above, can also have consumer acceptable lather properties. Lather can be measured in accordance with the Cylinder Method described below. Compositions may have a lather volume of about 300 mL, about 400 mL, about 500 mL, about 600 mL, about 700 mL, or more. Compositions may have a lather density of about 0.03 g/cc, about 0.04 g/cc, about 0.05 g/cc, 0.055 g/cc, 0.06 g/cc, 0.065 g/cc, or more. Compositions may have a lather mass of about 20 g, about 25 g, about 30 g, about 35 g, about 40 g, about 45 g, or more.

In accordance with the above, a cleansing composition comprises a surfactant, a hydric solvent, perfume, and water. Additionally, optional ingredients may also be included as noted herein, for example, preservatives, thickeners, hydrophobic oils, pH modifiers, additives, soap, etc. Optional ingredients can be include at a level of about 0.1% to about 5%, by weight of the composition, for example. The cleansing composition is not in the form of a ringing gel. The cleansing composition can be in the form of a microemulsion or may contain a microemulsion phase. At least a portion of the cleansing composition may become a microemulsion upon dilution with water of about 2:1 or about 3:1 by weight (water:composition) to about 10:1 by weight (water: composition).

A. Surfactant

A rinse-off cleansing composition includes surfactant. Surfactants can provide a cleaning benefit, lather properties, and rheology properties to the compositions. The surfactant may be a single surfactant or a combination of multiple surfactants. In addition, a surfactant may be branched, linear, or a combination thereof. A composition may comprise from about 20% to about 34%, from about 20% to about 32%, from about 20% to about 30%, from about 22% to about 30%, or from about 24% to about 28%, by weight of the composition, of surfactant. The previous weight percentages of surfactant in the composition include primary surfactant and a cosurfactant.

The surfactant may be anionic, zwitterionic, amphoteric, nonionic, or a combination thereof. The surfactant may include a first surfactant and a cosurfactant. The rinse-off cleansing composition may include from about 14% to about 34%, from about 15% to about 30%, from about 15% to about 25%, from about 16% to about 30%, from about 15% to about 20%, or from about 17% to about 25%, by weight of the composition, of an anionic surfactant.

The anionic surfactant can be linear or branched. The anionic surfactant can contain any counterion such as sodium, potassium, ammonium, triethanolamine, etc. The hydrocarbon chain can be an olefin or be branched or linear or cyclic, such as alkyl benzenes, and generally has between 10 and 20 carbons or 12 to 16 carbons. The anionic surfactant can comprise ethylene oxide groups, such as one EO, or two EO, or three EO, e.g., and can be a sulfate, sulfonate or carboxylate, including acidic sulfonates such as sulfosuccinates. Some exemplary anionic surfactants include a sulfate, an alkyl ether sulfate, an alkyl ether sulfate with about 0.5 to about 5 ethoxylate groups, sodium trideceth -2 sulfate, or a combination thereof.

Suitable anionic surfactants can include, for example, sodium trideceth sulfate and sodium laureth sulfate. These materials can have varying levels of ethoxylation. Thus, the levels of ethoxylation are represented by an (n), for example, sodium trideceth-n sulfate. n can range from about 0.5 to about 5. Some exemplary anionic surfactants are sodium trideceth-2 sulfate, sodium trideceth-3 sulfate, sodium laureth-1 sulfate, sodium laureth-2 sulfate, sodium laureth-3 sulfate, or combinations thereof.

The rinse-off cleansing composition may include from about 1% to about 15%, from about 2% to about 10%, or from about 4% to about 8%, by weight of the composition, of a cosurfactant. The cosurfactant may be, for example, zwitterionic surfactant, amphoteric surfactant, nonionic surfactant, or a combination thereof. Suitable amphoteric or zwitterionic surfactants can include those described in U.S. Pat. Nos. 5,104,646 and 5,106,609.

Additional amphoteric detersive surfactants suitable for use in the rinse-off cleansing compositions can include those surfactants broadly described as derivatives of aliphatic secondary and tertiary amines in which an aliphatic radical can be straight or branched chain and wherein an aliphatic substituent can contain from about 8 to about 18 carbon atoms such that one carbon atom can contain an anionic water solubilizing group, e.g., carboxy, sulfonate, sulfate, phosphate, or phosphonate. Examples of compounds falling within this definition can be sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and products described in U.S. Pat. No. 2,528,378. Other examples of amphoteric surfactants can include sodium lauroamphoacetate, sodium cocoamphoacetate, disodium lauroamphoacetate disodium cocodiamphoacetate, and mixtures thereof. Amphoacetates and diamphoacetates can also be used.

Zwitterionic surfactants suitable for use in the rinse-off cleansing compositions are well known in the art, and include those surfactants broadly described as derivatives of aliphatic quaternary ammonium, phosphonium, and sulfonium compounds, in which aliphatic radicals can be straight or branched chains, and wherein an aliphatic substituent can contain from about 8 to about 18 carbon atoms such that one carbon atom can contain an anionic group, e.g., carboxy, sulfonate, sulfate, phosphate, or phosphonate. Other zwitterionic surfactants can include a betaine, like an alkyl betaine or alkyl amidopropyl betaine, like cocoamidopropyl betaine.

Nonionic surfactants suitable for use can include those selected from the group consisting of alkyl ethoxylates, alkyl glucosides, polyglucosides (e.g., alkyl polyglucosides, decyl polyglucosides), polyhydroxy fatty acid amides, alkoxylated fatty acid esters, sucrose esters, amine oxides, or mixtures thereof. Some exemplary nonionic surfactants can include cocoamide monoethanolamine, decyl glucoside, or a combination thereof.

B. Perfume

A rinse-off cleansing composition includes a perfume. A composition may comprise from about 4% to about 25%, from about 4% to about 30%, from about 5% to about 20%, from about 6% to about 15%, from about 6% to about 30%, from about 7% to about 25%, from about 8% to about 20%, from about 8% to about 15%, from about 4% to about 15%, or from about 4% to about 10%, by weight of the composition, of perfume.

Perfume may include solvents such as triethyl citrate, isopropyl myristate, dipropylene glycol, or others, to help, for example, with the miscibility of the perfume molecules with each other or to reduce cost. Generally these perfume solvents provide minimal or negligible effects on surfactant compositions as a whole due to the low amount of perfume in the total composition and the amount of solvent in a perfume can be ignored. However, when solvent in the perfume accounts for more than about 5 wt % of the total hydric solvent in the cleansing composition, it should be accounted for. For example, when a perfume containing 10% hydric solvent is added to a cleansing composition at a level of 10 wt. % and the composition has 10 wt. % of added hydric solvent, the 1 wt. % of hydric solvent from the perfume accounts for a 9% increase in hydric solvent in the cleansing composition (1/11). Since this is more than a 5% change in the hydric solvent in the composition, it is important. In this case, hydric solvent from the perfume is added (mathematically) to the hydric solvent from other sources added to the composition; and perfume is considered to comprise only the scented molecules and not the solvent, which is subtracted from the wt % perfume in the composition.

In addition, the weight ratio of perfume to surfactant can impact the ability of the composition to provide an enhanced fragrance benefit. Without being limited by theory, it is believed at least some of the perfume benefits, like bloom and residual scent are derived from an abundance of perfume on the basis of its relation to the surfactant due at least in part to the interaction of the perfume with surfactant as the composition is diluted. Perfume is soluble in surfactant micelles only to about 25% by weight of the surfactant. Above this level, the composition can become unstable unless steps are taken to form a phase to accept the abundance of perfume. However, forming those phases for stability of the perfume circles the composition back to where the perfume is bound within the composition and difficult to release. As such, a rinse-off cleansing composition comprises from about 10% 12%, 15%, 20%, 25%, 30% 35%, 40%, 50%, 70%, to about 30%, 40%, 50%, 60%, 70%, 90%, 100%, or 150%, by weight of the surfactant, of perfume.

Perfumes generally contain a broad range of perfume molecules (PRM) having diverse properties. It is an oversimplification to suggest all of the perfume is in a particular location, like in the core of a microemulsion. The real picture is more complex, with perfume molecules in dynamic equilibrium and structures such as micelles and microemulsions can be percolating. Further, some perfume molecules may favor being among surfactant tails or even in the aqueous phase instead of the microemulsion core. In short, all perfume molecules within a perfume mixture do not behave identically. Certain generalizations are useful to explain observed behaviors without inferring that all molecules in a perfume behave identically. For our purposes, a broad array of perfume molecules in a perfume mixture are analyzed by averaging or summing their performance Certain perfume features may also impact perfume benefits, such as the proportion of perfume molecules within a volatility or molecular weight range. In general, Kovats Index (KI) is a useful parameter to differentiate perfume molecules. Perfume molecules having KI less than 1100 can be considered high blooming molecules; those having KI greater than 1400 can be considered high skin partitioning molecules; and those between (KI of 1100-1400) can be considered middle perfume notes which generally favor neither bloom nor skin partitioning, but contribute to some extent in both.

Perfume can be tailored to enhance features of the compositions. For example, while the compositions, including diluted compositions during use, can have a high activity coefficient, perfume molecules may selectively evaporate to enhance bloom or partition into the skin depending on their individual vapor pressure. It has surprisingly been discovered that the weight percentage of middle notes can impact the fragrance expression of the composition for the initial scent, for bloom and delivery on the skin. Particularly, better expression of the perfume is accomplished when the weight percentage of middle notes is restricted. For example, the composition may comprise a perfume, wherein the weight percentage of the perfume components having a Kovats Index of about 1100 to about 1700 comprises from about 0% to about 70%, from about 5% to about 50%, from about 5% to about 30%, or from about 5% to about 20%, by weight of the perfume.

In addition, it has also been discovered that the weight percentages of the perfume raw materials in a perfume composition can provide a strong rheological effect on the rinse-off cleansing composition. The wt % proportion of low, mid and high KI materials in the perfume impacts the elastic and viscous modulus of the composition as well as the viscosity. In general having a greater proportion of low KI materials results in a reduction in G' and G" and a lower tan delta (ratio of G"/G'). The following models of G' and G" were developed based on samples containing various proportions of low, mid and high KI materials and is a demonstration of the impact of KI on rheological properties for an exemplary concentrated body wash composition. G'=637.5−(1.118*wt % of Low KI Materials in a perfume)+(2.879*wt % proportion of Mid KI Materials in a perfume) and G"=7.510+(0.4056*wt % of Mid KI Materials in a perfume)+(0.6140*wt % of High KI materials in a perfume).

C. Solvent

A rinse-off cleansing composition includes a solvent. A rinse-off cleansing composition may comprise from about 3% to about 20%, from about 4% to about 18%, from about 5% to about 16%, from about 5% to about 15%, from about 6% to about 14%, or from about 4% to about 10%, by weight of the composition, of the solvent.

The solvent can be a hydric solvent. Examples of acceptable hydric solvents include dipropylene glycol (a glycol ether), diethylene glycol, dibutylene glycol, hexylene glycol, butylene glycol, pentylene glycol, heptylene glycol, propylene glycol, a polyethylene glycol having a weight average molecular weight below about 500, or a combination thereof. One example of a polyethylene glycol is PEG 300. Isomers are included in the generally descriptive solvents listed, for example, butylene glycol is meant to included 1,2-butanediol and 1,3-butanediol and 1,4-butanediol. When solvents are solid in the pure form (e.g., 1,6-hexanediol), they can be melted during the making process and are effective hydric solvents. The composition comprises at least 3%, 4%, 5%, 6%, 8%, 10%, or 12%, to about 10%, 12%, 15%, 20%, 25%, 30%, 35%, or 40%, by weight of the composition, of hydric solvent.

In addition, a cleansing composition may comprise from about 8%, 10%, 12%, 14%, 16%, 17%, 20%, 25%, 30%, 40%, 50%, or 60%, to about 40%, 50%, 60%, 70%, 80%, 90%, or 100%, or any combination thereof, by weight of the surfactant, of hydric solvent. For example, a cleansing composition can have 6%, by weight of the composition, of hydric solvent, and 44.5%, by weight of the composition, of surfactant. Hydric solvent levels can be expressed as a percent of the surfactant because the solvent molecules can engage with the surfactant molecules.

An intermediate level of hydric solvent can be used to deliver both a combination of exemplary rheology and perfume delivery properties. Thus, the hydric solvent can be from about 10% to about 40%, from about 12% to about 40%, from about 15% to about 35%, from about 17% to about 35%, from about 20% to about 30%, expressed as a weight percent of the surfactant.

A solvent may also comprise a non-hydric solvent. Examples of non-hydric solvents include propylene carbonate, butanol, pentanol, hexanol, propylene glycol ethers, butyl butanoate, propyl propanoate, isopropyl propanoate, or a combination thereof. One example of a propylene glycol ether is propylene glycol monomethylether. The non-hydric solvent may comprise less than about 25%, 20%, 15%, 10%, or 5%, by weight of the solvent.

D. Water

A rinse-off cleansing composition includes water. Water may come in with other components or may be added as free water. A rinse-off cleansing composition may comprise from about 10% to about 73%, from about 20% to about 70%, from about 30% to about 70%, from about 40% to about 65%, from about 50% to about 70%, or from about 50% to about 65%, by weight of the composition, of water.

In addition, the total weight percent of water and solvent can be important in the composition since this defines the amount of solvent phase in which the microemulsion or surfactant structures are distributed. The total amount of solvent phase (approximately, the additive inverse generally of the surfactant level) is a key driver of surfactant phases due to proximity of surfactants. Thus, the composition may comprise from about 13% to about 93%, from about 20% to about 90%, from about 30% to about 85%, from about 40% to about 75%, by weight of the composition, of the combination of water and solvent.

E. Rheology—Viscoelasticity and Viscosity

The rheological properties of rinse-off cleansing compositions can be characterized by viscoelastic parameters and a viscosity. The rheology of a composition can be defined by its G' and G" values, relating to the composition's structure. G' and G" are measured in accordance with the rheological properties method discussed herein. G' and G" describe a cleansing compositions elastic and viscous response to applied stress, characterizing how the material acts when dispensed from a bottle, sitting on the consumers implement or hand, and how a product spreads on application. It also impacts a consumer's perception of the product, for instance products with low G' values flow too readily in use and are associated in consumer perception and can be perceived as dilute. personal cleansing products, Conversely products with a high G' are associated in consumer perception with concentrated personal cleansing products. The cleansing composition may have a G' at about 1 Hz of about 25 Pa to about 3000 Pa; from about 50 Pa to about 2500 Pa, from about 100 Pa to about 1500 Pa, or from about 150 Pa to about 1000 Pa. The cleansing composition may have a G" at about 1 Hz of about 20 Pa to about 250 Pa; from about 35 Pa to about 200 Pa, from about 40 Pa to about 150 Pa, or from about 50 Pa to about 100 Pa.

In addition, the cleansing composition should have a viscosity sufficient to allow it to be dispensed from a package onto an implement or directly onto the skin. The viscosity of a rinse-off cleansing composition is measured in accordance with the rheological properties method discussed herein. The cleansing composition may have a viscosity at about 0.10 l/sec of about 10 PaS to about 1200 PaS; from about 20 PaS to about 1000 PaS, from about 30 PaS to about 500 PaS, or from about 40 PaS to about 300 PaS. The cleansing composition may have a viscosity at about 1 l/sec of about 1 PaS to about 30 PaS; from about 1 PaS to about 20 PaS, from about 1 PaS to about 15 PaS, or from about 1 PaS to about 10 PaS.

Compositions can also be highly shear thinning, having a viscosity ratio of less than about 0.20, or 0.10, or even less than 0.05, which is the ratio of the viscosity at 1 l/sec divided by the viscosity at 0.10l/sec.

F. Preservatives

Liquid cleansing compositions often have a high water activity (i.e. about 0.95 or more). Water activity describes the availability of water within a composition to support various chemical and biological processes requiring water. Compositions with high water activity can allow growth of microorganisms and therefore generally require preservatives. For example, bacteria can grow at a water activity of about 0.90 or above and fungus can grow at a water activity of about 0.70 or above. Below these water activities, microorganisms generally dehydrate and die.

The rinse-off cleansing compositions as noted herein can have a low water activity, less than about 0.90. This low water activity allows the compositions to naturally resist the growth of microorganisms and thus utilize minimal or even no, preservative. In addition, the use of high levels (5 wt. % or more) of glycols, like dipropylene glycol, can also help to prevent the growth of microorganisms and further support a composition which needs minimal or even no, preservative.

G. Hydrophobic Oils

The rinse-off cleansing composition may comprise a hydrophobic oil. Hydrophobic oil can help form a microemulsion phase due to low solubility in the palisade layer of micelles, to further enhance bloom and deposition on skin. The rinse-off cleansing composition may comprise from about 0% to about 25%, from about 2% to about 20%, or from about 3% to about 15% by weight of the composition, of a hydrophobic oil. Exemplary hydrophobic oils can include, for example, isopropyl myristate, isostearyl isostearate, behenyl behenate, triglycerides such as soybean oil, hydrocarbon such as mineral oil, or combinations thereof.

H. Additives

The rinse-off cleansing composition may comprise an additive. Additives are materials that are at least partially soluble in the perfume. It is believed that additives which are at least partially soluble in the perfume will also see a deposition benefit. Additives which are at least 5 wt %, or at least 10 wt %, or at least 20 wt % miscible with perfume may be employed to increase delivery of the additives to the skin or hair. Some examples of classes of material that can be soluble in the perfume are skin actives, vitamins, antibacterials, antifungals, chelants, or combinations thereof.

Examples of skin actives which can be included are sunscreens; anti-acne medicaments; antioxidants; skin soothing agents, skin healing agents; essential oils, skin sensates, anti-wrinkle medicaments, or mixtures thereof.

Some examples of skin soothing agents can include, for example, aloe vera, allantoin, bisabolol, dipotassium glycyrrhizinate, or combinations thereof.

Examples of vitamins which can be included are Vitamin A (e.g., beta carotene, retinoic acid, retinol, retinoids, retinyl palmitate, retinyl proprionate, etc.), Vitamin B (e.g., niacin, niacinamide, riboflavin, pantothenic acid, etc.), Vitamin C (e.g., ascorbic acid, etc.), Vitamin D (e.g., ergosterol, ergocalciferol, cholecalciferol, etc.), Vitamin E (e.g., tocopherol acetate, tocopherol nicotinate, etc.), Vitamin K (e.g., phytonadione, menadione, phthiocol, etc.), or combinations thereof.

Examples of antibacterials and/or antifungals which can be included are glycolic acid, lactic acid, phytic acid, N-acetyl-L-cysteine, phenoxyethanol, phenoxypropanol, phenoxyisopropanol, zinc pyrithione, octopirox (piroctone olamine), climbazole, ketoconazole, thymol, terpineol, essential oils, or combinations thereof.

Examples of chelants which can be included are 2-aminoethyl phosphoric acid (AEP), N-phosphonomethyl aminodiacetic acid (PMIDA), 1-hydroxyethane-1,1-diphosphonic acid (HEDP), amino tris(methylene phosphonic acid) (ATMP), ethylenediamine tetra(methylene phosphonic acid) (EDTMP), diethylenetriamine penta(methylene phosphonic acid) (DTPMP), phytic acid, nitrilotrimethylene phosphonic acid (NIP), 2-hydroxypyridine oxide (HPNO), or combinations thereof.

The rinse-off cleansing composition may comprise from about 1% to about 20%, from about 2% to about 10%, or from about 3% to about 8%, by weight of the composition, of an additive.

I. Thickeners

The rinse-off cleansing composition may comprise from about 0.1% to about 4% by weight of the composition of a thickener. Preferred thickeners are hydrophilic such as cellulose derivatives, hydrophobically modified celluloses, starches and starch derivatives, polyacrylates including hydrophobically modified polyacrylates and polyacrylamides, bacterial polymers such as xanthan gum, tree and plant gums such as guar, insoluble thickeners such as cellulose.

J. Soap

Rinse-off cleansing compositions as described herein may also comprise soap.

K. Packaging

Compositions can be dispensed from a squeezable package with an orifice, such as a conventional body wash or shampoo package. The package can be a compact package, i.e., contain less than about 250 ml, or 200 ml, or 150 ml of volume to signal the contents are concentrated.

The shear thinning compositions can be dispensed from a package with a slit valve orifice or other flexible orifice, which is generally cut from a silicone elastomeric material and inserted into an orifice housing. When the composition has a low viscosity, less than about 0.25 PaS at 1 l/sec, it can be dispensed from a foaming package such as a pump foamer. Compositions can also be dispensed from liquid pump packages.

L. Methods

In addition to the compositional elements and parameters noted above, it is believed there are also some inventive benefits and/or uses to the compositions which are set out as methods below. For the sake of brevity, all of the compositional elements and parameters noted above are not repeated herein, but can be used within the methods where relevant.

A method of enhancing fragrance of a rinse-off cleansing composition before use, comprising, combining: a) from about 20% to about 34%, by weight of the composition, of surfactant; b) from about 4% to about 30%, by weight of the composition, of a perfume, wherein the weight percent of perfume is from about 10% to about 90%, by weight of the surfactant; c) from about 3% to about 20%, by weight of the composition, of a solvent, wherein at least 3% of the solvent, by weight of the composition, comprises a hydric solvent and wherein the weight percent of the hydric solvent is from about 8% to about 60%, by weight of the surfactant; and d) from about 10% to about 73%, by weight of the composition, of water; wherein the rinse-off cleansing composition has a G' at 1 Hz of about 25 Pa to about 3000 Pa, and wherein the composition has a total GCMS count higher than that of a control where the solvent is replaced with water, when the total GCMS count is measured in accordance with the PHADD method at zero dilution. The composition may have a GCMS total count of about 10% more than the control, 15%, 20%, 25%, 50%, 75%, 100%, 150%, 200%, 250%, or even 300% more than the control.

A method of enhancing in-vitro bloom of a rinse-off composition, comprising, combining: a) from about 20% to about 34%, by weight of the composition, of surfactant; b) from about 4% to about 30%, by weight of the composition, of a perfume, wherein the weight percent of perfume is from about 10% to about 90%, by weight of the surfactant; c) from about 3% to about 20%, by weight of the composition, of a solvent, wherein at least 3% of the solvent, by weight of the composition, comprises a hydric solvent and wherein the weight percent of the hydric solvent is from about 8% to about 60%, by weight of the surfactant; and d) from about 10% to about 73%, by weight of the composition, of water; wherein the rinse-off cleansing composition has a G' at 1 Hz of about 25 Pa to about 3000 Pa and wherein the composition has a total GCMS peak area at the 3:1 dilution point which is at least 1.5 times greater than the GCMS peak area of the composition prior to dilution when measured in accordance with the PHADD method. The composition may have a GCMS peak area of about 1.75 times more than the composition prior to dilution, 2 times, 2.25 times, 2.5 times, 3 times, or even 4 times or more, more than the composition prior to dilution.

A method of enhancing fragrance of a rinse-off cleansing composition on skin or hair, comprising, combining: a) from about 20% to about 34%, by weight of the composition, of surfactant; b) from about 4% to about 30%, by weight of the composition, of a perfume, wherein the weight percent of perfume is from about 10% to about 90%, by weight of the surfactant; c) from about 3% to about 20%, by weight of the composition, of a solvent, wherein at least 3% of the solvent, by weight of the composition, comprises a hydric solvent and wherein the weight percent of the hydric solvent is from about 8% to about 60%, by weight of the surfactant; and d) from about 10% to about 73%, by weight of the composition, of water; wherein the rinse-off cleansing composition has a G' at 1 Hz of about 25 Pa to about 3000 Pa, and wherein the composition has a total GCMS count higher than that of a control where the solvent is replaced with water when the total GCMS count is measured in accordance with the PSHAM method. The composition may have a GCMS total count of about 10% more than the control, 15%, 20%, 25%, 50%, 75%, 100%, 150%, 200%, 250%, or even 300% more than the control.

A method of enhancing fragrance longevity of a rinse-off cleansing composition on skin or hair, comprising, combining: a) from about 20% to about 34%, by weight of the composition, of surfactant; b) from about 4% to about 30%, by weight of the composition, of a perfume, wherein the weight percent of perfume is from about 10% to about 90%, by weight of the surfactant; c) from about 3% to about 20%, by weight of the composition, of a solvent, wherein at least 3% of the solvent, by weight of the composition, comprises a hydric solvent and wherein the weight percent of the hydric solvent is from about 8% to about 60%, by weight of the surfactant; and d) from about 10% to about 73%, by weight of the composition, of water; wherein the rinse-off cleansing composition has a G' at 1 Hz of about 25 Pa to about 3000 Pa, and wherein the composition has a total GCMS count higher than that of a control where the solvent is replaced with water when the total GCMS count is measured in accordance with the PSHAM method at 1 hour after the initial application. The PSHAM method may also be evaluated at other time points, for example, 2 hours, 3 hours, 3.5 hours, 4hours, etc. after the initial application. The composition may have a GCMS total count of about 10% more than the control, 15%, 20%, 25%, 50%, 75%, 100%, 150%, 200%, 250%, or even 300% more than the control.

M. Exemplary Combinations

In this section, each paragraph further builds on the ones before it unless specifically limited.

A. An example of a rinse-off cleansing composition, can comprise: a)from about 20% to about 34%, by weight of the composition, of surfactant; b) from about 4% to about 30%, by weight of the composition, of a perfume, wherein the weight percent of perfume is from about 10% to about 90%, by weight of the surfactant; c) from about 3% to about 20%, by weight of the composition, of a solvent, wherein at least 3% of the solvent, by weight of the composition, comprises a hydric solvent and wherein the weight percent of the hydric solvent is from about 8% to about 60%, by weight of the surfactant; and d) from about 10% to about 73%, by weight of the composition, of water; wherein the rinse-off cleansing composition has a G' at about 1 Hz of about 25 Pa to about 3000 Pa.

B. The rinse-off cleansing composition of paragraph A, wherein the composition comprises from about 20% to about 32%, from about 20% to about 30%, from about 22% to about 30%, or from about 24% to about 28%, by weight of the composition, of surfactant.

C. The rinse-off cleansing composition of paragraphs A and B, wherein the surfactant comprises from about 14% to about 34%, from about 15% to about 30%, from about 16% to about 30%, or from about 17% to about 25%, by weight of the composition, of a first surfactant.

D. The rinse-off cleansing composition of paragraph C, wherein the first surfactant comprises an anionic surfactant.

E. The rinse-off cleansing composition of paragraph D, wherein the anionic surfactant comprises a sulfate, an alkyl ether sulfate, an alkyl ether sulfate with about .5 to about 5 ethoxylate groups, or sodium trideceth-2 sulfate.

F. The rinse-off cleansing composition of paragraphs A-E, wherein the surfactant comprises sodium trideceth-2 sulfate, sodium trideceth-3 sulfate, sodium laureth-1 sulfate, sodium laureth-2 sulfate, sodium laureth-3 sulfate, or combinations thereof.

G. The rinse-off cleansing composition of paragraphs A-F, wherein the surfactant further comprises from about 1% to about 15%, from about 2% to about 10%, or from about 4% to about 8%, by weight of the composition, of a cosurfactant.

H. The rinse-off cleansing composition of paragraph G, wherein the cosurfactant comprises a zwitterionic surfactant, an amphoteric surfactant, a nonionic surfactant, or a combination thereof.

I. The rinse-off cleansing composition of paragraphs G and H, wherein the cosurfactant comprises a betaine, an alkyl amidopropyl betaine, or cocoamidopropyl betaine.

J. The rinse-off cleansing composition of paragraphs A-I, wherein the composition comprises from about 4% to about 25%, from about 5% to about 20%, or from about 6% to about 15%, by weight of the composition, of the perfume.

K. The rinse-off cleansing composition of paragraphs A-J, wherein the perfume has from about 0% to about 50%, from about 5% to about 30%, from about 5% to about 20%, from about 5% to about 10%, by weight of the perfume, of perfume raw materials with a Kovats index from about 1100 to about 1700.

L. The rinse-off cleansing composition of paragraphs A-K, wherein the composition has from about 4% to about 18%, from about 5% to about 16%, from about 5% to about 15%, or from about 6% to about 14%, by weight of the composition, of the polar solvent.

M. The rinse-off cleansing composition of paragraphs A-L, wherein the hydric solvent comprises dipropylene glycol, diethylene glycol, dibutylene glycol, hexylene glycol, butylene glycol, pentanediol, heptanediol, propylene glycol, a polyethylene glycol having a weight average molecular weight below about 500, or a combination thereof.

N. The rinse-off cleansing composition of paragraphs A-N, wherein the composition comprises from about 20% to about 70%, from about 30% to about 70%, from about 40% to about 65%, or from about 50% to about 65%, by weight of the composition, of water.

O. The rinse-off cleansing composition of paragraphs A-N, wherein the composition comprises from about 13% to about 93%, from about 20% to about 90%, from about 30% to about 85%, or from about 40% to about 75%, by weight of the composition, of the combination of water and polar solvent.

P. The rinse-off cleansing composition of any preceding paragraph, wherein the composition has a G' at 1 Hz of about 50 Pa to about 2500 Pa, from about 100 Pa to about 1500 Pa, or from about 150 Pa to about 1000 Pa.

Q. The rinse-off cleansing composition of paragraphs A-P, wherein the composition has a G" at 1 Hz of about 20 Pa to about 250 Pa, from about 35 Pa to about 200 Pa, from about 40 Pa to about 150 Pa; or from about 50 Pa to about 100 Pa.

R. The rinse-off cleansing composition of paragraphs A-Q, wherein the composition has a viscosity at a shear rate of 0.01 l/sec of about 10 PaS to about 1200 PaS, from about 20 PaS to about 1000 PaS, from about 30 PaS to about 500 PaS, or from about 40 PaS to about 300 PaS, when measured in accordance with the Viscosity Method.

S. The rinse-off cleansing composition of paragraphs A-R, wherein the composition has a viscosity at a shear rate of 10 l/sec of about 1 PaS to about 30 PaS, from about 1 PaS to about 20 PaS, from about 1 PaS to about 15 PaS, or from about 1 PaS to about 10 PaS, when measured in accordance with the Viscosity Method.

T. The rinse-off cleansing composition of paragraphs A-S, wherein the composition is stable at 40° C.

U. The rinse-off cleansing composition of paragraphs A-U, wherein the composition further comprises soap.

V. The rinse-off cleansing composition of paragraphs A-U, wherein the composition further comprises a hydrophobic oil.

W. The rinse-off cleansing composition of paragraph V, wherein the composition comprises from about 2% to about 20%, or from about 3% to about 15%, by weight of the composition, of the hydrophobic oil.

X. The rinse-off cleansing composition of paragraphs V and W, wherein the hydrophobic oil comprises isopropyl myristate, isostearyl isostearate, behenyl behenate, soybean oil, mineral oil, or combinations thereof.

Y. The rinse-off cleansing composition of paragraphs A-X, wherein the composition further comprises an additive.

Z. The rinse-off cleansing composition of paragraph Y, wherein the additive comprises a skin active, a vitamin, an antibacterial, an antifungal, a chelant, a pH regulator, or a combination thereof.

AA. The rinse-off cleansing composition of paragraphs A-Z, wherein the composition is liquid.

BB. The rinse-off cleansing composition of paragraphs A-AA, wherein the composition is not a ringing gel.

CC. The rinse-off cleansing composition of paragraphs A-BB, wherein the perfume is from about 10% to about 90%, from about 10% to about 50%, or from about 20% to about 40%, by weight of the surfactant.

DD. The rinse-off cleansing composition of paragraphs A-CC, wherein the weight percent of hydric solvent is from about 10% to about 40%, from about 12% to about 40%, from about 15% to about 35%, from about 17% to about 35%, or from about 17% to about 30%, by weight of the surfactant.

EE. The rinse-off cleansing composition of paragraphs A-DD, wherein the composition is a microemulsion or contains a microemulsion phase.

FF. The rinse-off cleansing composition of paragraphs A-EE, wherein at least a portion of the composition becomes a microemulsion upon dilution with water of about 3:1 by weight (water:composition) to about 10:1 by weight (water:composition).

GG. The rinse-off cleansing composition of paragraphs A-FF, wherein the solvent comprises dipropylene glycol.

HH. Another exemplary rinse-off cleansing composition, comprises: a) from about 15% to about 20%, by weight of the composition, of a first surfactant comprising sodium trideceth-2 sulfate; b) from about 4% to about 10%, by weight of the composition, of a perfume; c) from about 4% to about 10%, by weight of the composition, of dipropylene glycol; and d) from about 50% to about 70%, by weight of the composition, of water; wherein the rinse-off cleansing composition has a G' of about 25 Pa to about 3000 Pa.

II. The rinse-off cleansing composition of paragraph HH, wherein the composition further comprises from about 4% to about 10%, by weight of the composition, of a cosurfactant comprising cocoamidopropyl betaine.

JJ. The rinse-off cleansing composition of paragraphs HH and II, wherein the composition is a microemulsion or contains a microemulsion phase.

EXAMPLES

The inventive examples are prepared by weighing the components together into a Speedmixer pot, stirring by hand briefly to homogenize the fluids, and then speedmixing for 60 seconds at 2750 rpm.

|  | Ex. 1 |
|---|---|
| Sodium trideceth-2 sulfate | 18.14 |
| Cocoamidopropyl betaine | 6.7 |
| Dipropylene glycol | 5.88 |
| Water | qs |
| Citric acid | 0.27 |

-continued

|  | Ex. 1 |
| --- | --- |
| perfume | 6.33 |
| G' at 1 Hz (Pa) | 68.4 |
| Viscosity at 1 sec$^{-1}$ (PaS) | 10.6 |
| Total surfactant | 24.84 |
| Hydric solvent as percent of surfactant | 23.67 |
| Perfume as percent of surfactant | 25.48 |

Example: Delivery of Perfume to Skin from a Cleansing Composition

Delivery of perfume to the skin was measured for Ex. 1 and a control composition according to the PSHAM method using 4 subjects. One arm is washed with Ex. 1 and the opposing arm with the control (a micelle body wash comprising 9 wt % sodium laureth-3 sulfate, 1 wt % cocoamidopropyl betaine, 2.5 wt % sodium chloride and 1.08 wt % of the identical perfume). For the control, 10 ml of body wash was dosed into a wet puff, lathered for 15 seconds with the hands, used to wash the arm for 15 seconds, then rinsed for 15 seconds. For the inventive composition, 1.7 ml was used in the same manner The dramatic increase in total headspace counts collected over the arms with Ex. 1 versus the control illustrates an increase in the amount of perfume deposited on the skin during the cleansing process.

|  | Control arms | Ex. 1 arms |
| --- | --- | --- |
| Total headspace counts collected over arms at time zero (average of arms for 36 perfume components) | 14,867,000 | 38,941,000 |
| Ratio to control | 1 | 2.62 |

Rheology response surface at 37% total solids (<30% surfactant)

| Ex. # | STE-2-S | CAPB | total surfactant | perfume | DPG | water | G' at 1 Hz (Pa) | perfume as % of surfactant | hydric solvent as % of surfactant |
| --- | --- | --- | --- | --- | --- | --- | --- | --- | --- |
| 2 | 17.3 | 6.4 | 23.7 | 8.64 | 4.76 | qs | 276 | 36.5% | 20.1% |
| 3 | 17.7 | 6.5 | 24.2 | 7.29 | 5.41 | qs | 284 | 30.1% | 22.4% |
| 4 | 17.2 | 6.4 | 23.6 | 7.29 | 6.01 | qs | 68 | 30.9% | 25.5% |
| 5 | 18.5 | 6.9 | 25.4 | 6.39 | 5.11 | qs | 207 | 25.2% | 20.1% |
| 6 | 18.1 | 6.7 | 24.8 | 6.3 | 5.9 | qs | 68 | 25.4% | 23.8% |
| 7 | 17.7 | 6.5 | 24.2 | 6.48 | 6.22 | qs | 57 | 26.8% | 25.7% |
| 8 | 17.4 | 6.4 | 23.8 | 6.3 | 6.8 | qs | 32 | 26.5% | 28.6% |
| 9 | 19.6 | 7.3 | 26.9 | 5.04 | 5.06 | qs | 33 | 18.7% | 18.8% |

Rheology response surface at 32% total solids (<25% surfactant)

|  | STE-2-S | CAPB | total surfactant | perfume | DPG | water | G' at 1 Hz (Pa) | viscosity at 1 1/sec (PaS) | perfume as % of surfactant | hydric solvent as % of surfactant |
| --- | --- | --- | --- | --- | --- | --- | --- | --- | --- | --- |
| 10 | 15.7 | 5.8 | 21.5 | 6.75 | 3.75 | qs | 261 | 13 | 31.4% | 17.4% |
| 11 | 16.4 | 6.1 | 22.5 | 5.85 | 3.65 | qs | 130 | 23.3 | 26.0% | 16.2% |
| 12 | 17.0 | 6.3 | 23.3 | 5.13 | 3.57 | qs | 89 | 14.2 | 22.0% | 15.3% |
| 13 | 15.9 | 5.9 | 21.8 | 6.075 | 4.175 | qs | 81 | 13.2 | 27.9% | 19.2% |
| 14 | 16.6 | 6.2 | 22.8 | 5.175 | 4.075 | qs | 40 | 7.5 | 22.7% | 17.9% |
| 15 | 15.3 | 5.7 | 21 | 6.3 | 4.7 | qs | 58 | 10.15 | 30.0% | 22.4% |
| 16 | 16.1 | 5.9 | 22 | 5.4 | 4.6 | qs | 37 | 6.73 | 24.5% | 20.9% |
| 17 | 16.8 | 6.2 | 23 | 4.5 | 4.5 | qs | 39 | 7.24 | 19.6% | 19.6% |
| 18 | 16.4 | 6.0 | 22.4 | 4.59 | 5.01 | qs | 19 | 6 | 20.5% | 22.4% |

Test Methods a) G' and G" Test Method

To measure the viscoelastic properties of a personal care composition, the viscous (G") and elastic (G') moduli, use a rheometer such as a AR G2 Rheometer (TA Instruments, DE, USA) with 1 degree cone upper geometry with a diameter of 40 mm and flat plate lower geometry with Peltier heating/cooling to control temperature. Place approximately 1 gram of personal care composition onto the lower test geometry and lower the upper geometry into position, lock the geometry and wipe away excess composition to create an even surface around the edge of the geometry. Conduct the oscillatory test over frequency range of 0.01 to 100 Hz, collecting 5 data points per decade, using a constant oscillatory stress of 0.5968 Pa and a temperature of 25° C. The tan delta is calculated as the ratio of G"/G'.

Record the G' and G" (Pa) at a frequency of 1 Hz.

b) Ultracentrifuge Test

Compositions are considered to be in a single phase when they do not separate into layers or phases when ultracentrifuged for 2 hours at 50,000 rpm in an ultracentrifuge at 40° C. (e.g., Beckman ultracentrifuge with swinging bucket rotor).

c) Viscosity Method

To measure the viscosity of a personal care composition use a rheometer such as an AR G2 Rheometer (TA Instruments, DE, USA) equipped with 1 degree cone upper geometry with a diameter of 40 mm and flat plate lower geometry equipped with Peltier heating/cooling to control temperature. Measurement can be conducted by placing approximately 1 gram of personal care composition onto the lower test geometry and lowering the upper geometry into position to the desired gap of 52 microns, wiping away any excess composition to create an even surface around the edge of the geometry. Conduct a continuous flow test at 25° C., controlling the shear rate and progressing from a shear rate of 0.01 to 100 1/sec over a time period of 3 minutes, running the test in log mode and collecting 15 points per decade. Record the viscosity (PaS) at the shear rates of interest, for the samples herein we have reported the viscosity at a shear rate of about 0.10 1/sec and about 1 1/sec, interpolating as needed to obtain values at shear rates.

d) Perfume Headspace Abundance During Dilution Method (PHADD)

1) Perfume Headspace Abundance for Neat Products

Unless otherwise indicated, all laboratory instruments are operated according to manufacturer's instructions. The following equipment is used: 20 mL headspace vials from Gerstel (Baltimore, Md.); timer; gas chromatograph (GC) Agilent model 6890 and Gerstel MPS-2 auto sampler; GC column J&W DB5-MS, 30 m×0.25 mm ID, 1.0 μm film thickness obtained from Agilent Technologies, Inc., Wilmington, Del., USA; carrier gas of ultra-pure helium, about 1 mL/min. flow rate; solid-phase microextraction injection port liner (0.75mm ID) from Supelco; and a model 5973 Mass Selective Detector obtained from Agilent Technologies, Inc., Wilmington, Del., USA having a source temperature of about 230° C., and a MS Quad temperature of about 150° C.

1 gram of cleansing composition is placed into a clean 20mL headspace vial and a stir bar is added to the vial. A polytetrafluroethylene cap is placed on the vial and hand tightened. The sample is allowed to equilibrate to establish equilibrium of the perfume molecules between the composition and the headspace. This generally takes at least 30 minutes at room temperature. The sample is then analyzed using an automated solid phase microextraction-gas chromatograph-mass spectrometer (SPME-GC-MS) analysis system.

Transfer the sample vials to the auto sampler tray to begin analysis. Start the sequence of sample loading and analysis. Each sample vial is taken by the auto sampler to the incubation chamber and held at 30° C. for 1 minute. The SPME fiber assembly is DVB/CAR/PDMS (50/30 um, 24 ga, 1 cm length). Sampling time is 1 minute. The samples are stirred at 500 rpm during SPME sampling. After sampling, the SPME fiber is injected into the GC injector. The injector temperature is about 270° C.

The GC-MS analysis is started. SPME desorption time is about 5 minutes. The following temperature program is used: i) an initial temperature of about 50° C. which is held for 0.5 minutes, and ii) increase the initial temperature at a rate of about 8° C./min until a temperature of about 275° C. is reached, hold at about 275° C. for 2.5 minutes. Perfume compounds are identified using the MS spectral libraries of John Wiley & Sons and the National Institute of Standards and Technology (NIST), purchased and licensed through Agilent. Chromatographic peaks for specific ions are integrated using the MassHunter software obtained from Agilent Technologies, Inc., Wilmington, Del., USA. To calculate the perfume headspace abundance, all of the area counts of the perfume molecules are added together.

2) Perfume Headspace Abundance for Diluted Product

For the perfume headspace abundance for diluted product, use the method above for neat product, except 1.0 g of product is combined with sufficient water to reach the desired level of dilution, usually between (0.5-5 g), a magnetic stir bar is added to each vial, and after the cap is in place, the vials are stirred via the magnetic bar for at least 30 minutes to equilibrate.

e) Perfumed Skin Headspace Abundance Method (PSHAM)

Unless otherwise indicated, all laboratory instruments are operated according to manufacturer's instructions. The following equipment is used: Stir Bar Sorptive Extraction Sampling Devices—Gerstel Twister, 2 cm in length with 1 mm PDMS (polydimethyl silicone) phase thickness; glass sampling cups with magnets to hold Twisters during sampling—about 35 mL in volume; timer; gas chromatograph (GC) Agilent model 7890 and Gerstel MPS-2 autosampler with thermal desorption unit (TDU) and cooled-on-column (CIS-4) temperature programmable inlet; GC column J&W DB5-MS, 30 m×0.25 mm ID, 1.00 um film thickness obtained from Agilent Technologies, Inc., Wilmington, Del., USA; carrier gas of ultra-pure helium, about 1 mL/min. flow rate; liquid nitrogen for injection port cryogenic cooling; Gerstel TDU injection port liners with glass wool; and a detector model 5975 Mass Selective Detector obtained from Agilent Technologies, Inc., Wilmington, Del., USA having a source temperature of about 230° C., and a MS Quad temperature of about 150° C.

Headspace samples are collected from panelists' arms that have been washed with test products and/or controls. The wash protocol includes: 1) adjusting water temperature to about 100° F. and water flow to about 1 gallon/min; 2) rinsing the arm under the water stream for about 5 seconds; 3) apply product of known weight on a puff which has been prewetted for 5 seconds with water; 4) lather product in the puff by hands for 10 seconds; 5) wash the entire forearm for 15 seconds using back and forth motion, then wait for about 15 seconds; 6) rinse the arm under the water stream for about 15 seconds; 7) pat dry the forearm using a paper towel; and then 8) proceed to sensory evaluation or analytical sampling.

The Twister device is held inside of the sampling cup with magnetic force while the cup is placed against panelists' arms for a period of 3 minutes. The Twister is then transferred to the thermal desorption tube and capped with a transport adapter.

To begin the analysis, transfer the Twister transport tubes to the autosampler tray and proceed with TDU-GC-MS analysis. Set-up the sequence of samples needing to be analyzed and start the sequence of sample loading and analysis. In this step, the Twister transport tube is taken by the autosampler to the thermal desorption unit where it is heated to about 250° C. and held at that temperature for about 5 minutes. Perfume materials that are thermally desorbed from the Twister are trapped by the liquid nitrogen cooled inlet, which is held at about −120° C. during desorption. The programmable temperature inlet is then heated 275° C. and held at that temperature for 3 minutes.

The GC-MS analysis run is started and the GC temperature program is initiated with mass spectrometer detection. The following temperature program is used: i) an initial temperature of about 50° C. which is held for 0.5 minutes, and ii) increase the initial temperature at a rate of about 8° C./min until a temperature of about 275° C. is reached, hold at about 275° C. for 5 minutes. Perfume compounds are identified using the MS spectral libraries of John Wiley & Sons and the National Institute of Standards and Technology (NIST), purchased and licensed through Agilent. Chromatographic peaks for specific ions are integrated using the MassHunter software obtained from Agilent Technologies, Inc., Wilmington, Del., USA. Abundance of perfume in the headspace over the skin is calculated by adding the area counts of all the perfume molecules. The relative enhancement of abundance of perfume in the headspace using test products over control products is obtained by the ratio of the total peak area counts. The PSHAM measurement may be repeated on the target surface at later time intervals to test for longevity of fragrance on the skin. These time intervals could be any desired, for example, 1 hour, 2 hours, 3 hours, 3.5 hours, 4 hours, etc. after the initial application.

f) Cylinder Method

Lather can be measured in accordance with the Cylinder Method. Lather volume is measured using a graduated cylinder and a rotating mechanical apparatus. A 1,000 ml graduated cylinder is used which is marked in 10 ml increments, has a height of 14.5 inches at the 1,000 ml mark from the inside of its base, and has a neck at its top fitted for a plastic insert cap (for example, Pyrex No. 2982). Moderately hard water is prepared with 1.5:1 ion ratio Ca/Mg by dissolving 1.14 grams calcium chloride dihydrate and 1.73 grams magnesium chloride hexahydrate into one U.S. gallon distilled water. The water is maintained at between 105-110° F. The graduated cylinder is heated to about the same temperature by flushing with excess tap water at the same temperature for about 15 seconds, then drying it outside and shaking briefly upside down to dry the interior. 100.0 grams of the moderately hard water at the indicated temperature is weighed directly into the graduated cylinder. The cylinder is clamped in a mechanical rotating device, which clamps the cylinder vertically with an axis of rotation that transects the center of the graduated cylinder. Using a 3- or 4-place metric balance, invert the plastic cap for the graduated cylinder onto the balance pan and weigh 0.500 grams of composition (for compositions less than 19% surfactant) to within 4 milligrams accuracy, using a holder to keep the cap level. When the surfactant level is 40% or greater, use 125 mg of composition (500 g/4). When it is between 30% and 39%, use 135 mg of composition, and when it is between 20% and 29% use 250 mg and for 19 wt % and below use 500 mg. Insert the cap into the graduated cylinder neck while being careful that all composition is now in the space in the cylinder interior. For compositions with very low viscosity which will not remain on the cap surface, 500 mg composition can be added directly to the graduated cylinder. Rotate the cylinder for 25 complete revolutions at a rate of about 10 revolutions per 18 seconds to create a lather and stop in a level, vertical position. When the cylinder stops in a vertical position, start a digital stopwatch. Observing the water draining at the bottom, record the time to the nearest second when the water height measures 50 cc, then 60 cc, then 70 cc and so on until at least 90 cc has drained. Measure and record the total height of the foam in the column interior, which is the lather volume. If the top surface of the lather is uneven, the lowest height at which it is possible to see halfway across the graduated cylinder is the lather volume (ml). If the lather is coarse such that a single or only a few foam cells ("bubbles") reach across the entire cylinder, the height at which at least about 10 foam cells are required to fill the space is the lather volume, also in ml up from the base. When measuring the lather height, bubbles that are larger than about 1 inch across at the top surface are considered free air and not lather. The measurement is repeated and at least three results averaged to obtain the lather volume. In a spreadsheet, calculate the lather density at each observed time point as the volume of foam (total height minus water height) divided by the weight of the foam (100.5 grams minus the weight of water observed, using a density of 1.00 g/cc for water). Fit the 3 time points closest to (ideally, also bracketing) 20 seconds to a $2^{nd}$ order polynomial equation. Solve the equation for the lather density at 20 seconds, which is the lather density of the composition. Multiply the lather volume by the lather density to obtain the lather mass, in grams.

The entire process should take less than about 3 minutes in order to maintain desired temperature.

g) Stability Test

A composition is filled into a 4 fl. oz. glass jar with minimal headspace and capped, placed in a dark room maintained at 40° C. for 3 months. A composition is stable if there is minimal visual sign of phase separation and the viscosity changes by less than about 90% from the original viscosity.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of cleansing skin and/or hair comprising:
   a) providing a bottle containing a cleansing composition, comprising:
      i) about 20% to about 34%, by weight of the composition, of surfactant comprising:
         (1) about 15% to about 25%, by weight of the composition, of comprising sodium trideceth-n sulfate, wherein n is about 1 to about 3;
         (2) about 1% to about 10%, by weight of the composition, of a cosurfactant comprising cocoamidopropyl betaine;
      ii) about 4% to about 30%, by weight of the cleansing composition, of a perfume, wherein the weight percent of perfume is from about 10% to about 90%, by weight of the surfactant;
      iii) about 3% to about 20%, by weight of the cleansing composition, of dipropylene glycol,;
      iv) about 10% to about 73%, by weight of the cleansing composition, of water;
      wherein the cleansing composition in the bottle has a G' at 1 Hz of about 25 Pa to about 3000 Pa;
      wherein the cleansing composition in the bottle does not comprise a microemulsion;
      wherein the cleansing composition in the bottle comprises a gel structurant comprising a lamellar phase;
   b) applying the cleaning composition to the skin and/or hair;
   c) rinsing the product from the skin and/or hair;
      wherein during applying and/or rinsing, the cleansing composition is diluted with water and at least a portion of the cleansing composition becomes a microemulsion;
      wherein the cleansing composition provides enhanced scent during cleansing and/or residual scent on the skin after cleansing.

2. The method of claim 1, wherein the cleansing composition comprises about 4% to about 8%, by weight of the composition, of the cosurfactant.

3. The method of claim 2, wherein the cleansing composition comprises from about 4% to about 10%, by weight of the composition, of the perfume.

4. The method of claim 1, wherein the perfume comprises from about 5% to about 30%, by weight of the perfume, of perfume raw materials with a Kovats index from about 1100 to about 1700.

5. The method of claim 1, wherein the composition comprises about 8% to about 16%, by weight of the composition, of the solvent.

6. The method of claim 1 wherein the hydric solvent is dipropylene glycol.

7. The method of claim 1, wherein the composition comprises about 30% to about 61%, by weight of the composition, of water and solvent.

8. The method of claim 1, wherein the composition in the bottle has a G' at 1 Hz of about 50 Pa to about 2500 Pa, a G" at 1 Hz of about 20 Pa to about 250 Pa, or a combination thereof.

9. The method of claim 1, wherein the microemulsion forms when the cleansing composition is diluted to have a weight ratio of water:composition of about 3:1 to about 10:1.

10. The method of claim 1, wherein the cleansing composition comprises a lather volume of more than 300 mL according to the Cylinder Method.

11. A method of cleansing skin and/or hair comprising:
    a) providing a bottle containing a cleansing composition, wherein the cleansing composition comprises:
       i) about 20% to about 34%, by weight of the cleansing composition, of a surfactant comprising about 15% to about 30% of a branched anionic surfactant selected from the group consisting of sodium trideceth-2 sulfate, sodium trideceth-3, and combinations thereof; and about 2% to about 10% of a zwitterionic surfactant comprising comprising cocoamidopropyl betaine;
       ii)) about 4% to about 30%, by weight of the cleansing composition, of a perfume, wherein the weight percent of perfume is from about 10% to about 90%, by weight of the surfactant;
       iii) about 3% to about 20%, by weight of the cleansing composition, of dipropylene glycol; and
       iv) about 10% to about 73%, by weight of the cleansing composition, of water;
       wherein the cleansing composition in the bottle has a G' at 1 Hz of about 25 Pa to about 3000 Pa;
       wherein the cleansing composition in the bottle does not comprise a microemulsion;
       wherein the cleansing composition in the bottle comprises a gel structurant comprising a lamellar phase;
    b) applying the cleaning composition to the skin and/or hair;
    c) rinsing the product from the skin and/or hair;
       wherein during dispensing, applying, and/or rinsing the cleansing composition is diluted with water and at least a portion of the cleansing composition becomes a microemulsion;
       wherein the microemulsion forms when the cleansing composition is diluted to have a weight ratio of water:composition of about 3:1 to about 10:1 ;
       wherein the cleansing composition provides enhanced scent during cleansing and/or residual scent on the skin after cleansing.

12. The method of claim 11, wherein the cleansing composition in the bottle comprises a G' of about 25 Pa to about 3000 Pa.

13. The method of claim 11, wherein the branched anionic surfactant comprises sodium trideceth-2 sulfate and the zwitterionic surfactant comprises cocoamidopropyl betaine.

14. A method of cleansing skin and/or hair comprising:
    a) providing a bottle containing a cleansing composition, wherein the cleansing composition comprises:
       i) about 20% to about 34%, by weight of the composition, of a surfactant comprising sodium trideceth-n sulfate, wherein n is about 1 to about 3, and about 1% to about 10%, by weight of the composition, of cocoamidopropyl betaine;
       ii) about 4% to about 30%, by weight of the composition, of a perfume, wherein the weight percent of perfume is about 10% to about 90%, by weight of the surfactant;
       iii) about 3% to about 20%, by weight of the composition, of dipropylene glycol wherein the weight percent of the dipropylene glycol is from about 8% to about 60%, by weight of the surfactant; and
       iv) from about 10% to about 73%, by weight of the composition, of water;

wherein the cleansing composition in the bottle has a G' at 1 Hz of about 25 Pa to about 3000 Pa;

wherein the cleansing composition in the bottle does not comprise a microemulsion;

wherein the cleansing composition in the bottle comprises gel structurant comprising a lamellar phase;

b) applying the cleaning composition to the skin and/or hair;

c) rinsing the product from the skin and/or hair;

wherein during applying and/or rinsing the cleansing composition is diluted with water and at least a portion of the cleansing composition spontaneously becomes a microemulsion;

wherein the cleansing composition provides enhanced scent during cleansing and/or residual scent on the skin after cleansing.

15. The method of claim 14, wherein the anionic branched surfactant comprises sodium trideceth-2 sulfate.

* * * * *